(12) United States Patent
Lorenzi et al.

(10) Patent No.: US 6,323,316 B1
(45) Date of Patent: Nov. 27, 2001

(54) FIBROBLAST GROWTH FACTOR RECEPTOR ACTIVATING GENE 1 AND RELATED COMPOSITIONS AND METHODS

(75) Inventors: Matthew V. Lorenzi, Philadelphia, PA (US); Toru Miki, North Bethesda, MD (US)

(73) Assignee: The United States of America as represented by the Secretary of the Department of and Human Services, Wsahington, DC (US)

( * ) Notice: Subject to any disclaimer, the term of this patent is extended or adjusted under 35 U.S.C. 154(b) by 0 days.

(21) Appl. No.: 09/202,548

(22) PCT Filed: Jun. 18, 1997

(86) PCT No.: PCT/US97/10660

§ 371 Date: Dec. 15, 1998

§ 102(e) Date: Dec. 15, 1998

(87) PCT Pub. No.: WO97/48813

PCT Pub. Date: Dec. 24, 1997

Related U.S. Application Data

(60) Provisional application No. 60/020,009, filed on Jun. 18, 1996.

(51) Int. Cl.[7] .......................... C07K 14/00; C12P 21/06; C12N 15/09; C12N 15/63; C12N 5/00
(52) U.S. Cl. .................. 530/350; 435/69.1; 435/320.1; 435/325; 435/252.3; 536/23.5; 530/389.1; 530/388.85
(58) Field of Search ................ 530/388.85, 389.1, 530/350; 536/235, 231; 435/69.1, 320.1, 325, 252.3

(56) References Cited

FOREIGN PATENT DOCUMENTS

| WO 91/17183 | 11/1991 | (WO) . |
| WO 94/00599 | 1/1994 | (WO) . |
| WO 97/48813 | 12/1997 | (WO) . |

OTHER PUBLICATIONS

Dionne et al., Cloning and Expression of Two Distinct High–Affinity Receptors Cross–Reacting with Acidic and Basic Fibroblast Growth Factors, *EMBO Journal* 9:2685–2692 (1990).

Golub et al., Fusion of PDGF Receptor β to a Novel ets–like Gene, tel, in Chronic Myelomonocytic Leukemia with t(5;12) Chromosomal Translocation, *Cell Volume* 77:307–316 (1994).

Hattori et al., K–sam, an Amplified Gene in Stomach Cancer, Is a Member of the Heparin–Binding Growth Factor Receptor Gene, *Proc. Natl. Acad. Sci.*, USA 87:5983–5887 (1990).

Lee et al., Purification and Complementary DNA Cloning of a Receptor for Basic Fibroblast Growth Factor, *Science*, 245:57–60 (1989).

Lee et al., Comparative Expressed—Sequence–Tag Analysis of Differential Gene Expression Profiles in PC–12 Cells Before and After Nerve Growth Factor Treatment, *Proc. Natl. Acad. Sci.*, USA 92:8303–8307 (1995).

Lorenzi et al., FRAG1, a Gene that Potently Activates Fibroblast Growth Factor Receptor by C–Terminal Fusion Through Chromosomal Rearrangement, *Proc. Natl. Acad. Sci.*, USA 93:8956–8961 (1996).

Miki et al., Expression of cDNA Cloning of the KGF Receptor by Creation of a Transforming Autocrine Loop, *Science* 251:72–75 (1991).

Pasquale et al., Identification of a Developmentally Regulated Protein–Tyrosine Kinase By Using Anti–Phosphotyrosine Antibodies to Screen a cDNA Expression Library, *Proc. Natl. Acad. Sci.*, USA 86:5449–5453 (1989).

Sawyers C.L. and Denny, C.T., Chronic Myelomonocytic Leukemia: Tel–a–Kinase What Ets All About, *Cell* 77:171–173 (1994).

*Primary Examiner*—Elizabeth Kemmerer
*Assistant Examiner*—Janet L. Andres
(74) *Attorney, Agent, or Firm*—Klarquist Sparkman, LLP

(57) ABSTRACT

A novel gene designated as FRAG 1 and its encoded protein are disclosed. A fusion protein called FGFR2-ROS, which is formed by chromosomal rearrangement of rat FRAG1 with FGFR2, is also disclosed. Methods of producing FRAG1 protein, related fusion proteins, and antibodies against FRAG1 are disclosed, as are related pharmaceuticals and methods of using such nucleic acids, polypeptides, and antibodies.

35 Claims, 8 Drawing Sheets

```
                        770        780 784                          806        813
                        |          |   |                            |          |
FGFR2-WT     DRILTLTTNEEYLDLTQPLEQYSPSYPDTRSSCSSGDDSVFSPDPMPYEPCLPQYPHINGSVKT*
FGFR2-ET     DRILTLTTNEEYLDLSQPLEPYSPCYPDR*
FGFR2-ROS    DRILTPGSAPLATGVRPPSHHYLGPSAQDPSRHCGWRRGGALEPQTSFESLPCQLACGFESDKM...
```

FIGURE 2

```
    1                         CGCGCGGGCAGGTCTATGGGGAGGGACGAGGAGTCCCACTCTCT
   45 CTGCGGCAACGGTTGGCTGAGAAAGGGTCATGACGTCACACAGGGCCCTCGAAGAGGGCA
  105 GGTGAGTGGCTAGAGTAGTGAGCACCAAACAGCAGTGACGTTGGGTTCAGACCCCGCCCC
  165 TTTCCTTGGAGCGCGGAGACTCGCTACGGAAGCTTCGGCCAATCAGAAGGAAGACCCAAG
  225 GATGATATGGTGATGGCATGCAGCCAGAGGTAAAATGACAAGGTGACTTATTCGACATGT
  285 CAAAATCTTGTTTCCAGAGCTCTCTGACTGCTCTCACGTACTCAAAAATAGTGGGGACAG
                                                              W  G  Q
  345 AGCCGACCTGGGGAGGCTTGGCTTCAAGAGACGCTAGATTATAAAGAAAGCCAGGAGTCC
          S  R  P  G  E  A  W  L  Q  E  T  L  D  Y  K  E  S  Q  E  S
  405 CGGTCGCCAAAATGGGGAGGAGCCAGTGAAGAAACGGGCCCAGTTTCCTCTTTAAGACCC
          R  S  P  K  W  G  G  A  S  E  E  T  G  P  V  S  S  L  R  P
  465 ACCCCAGAGCGCTGGCCCCGCCTCACGCCGTTGCTGCTGCGACCCGCCCCCTTCCACTCG
          T  P  E  R  W  P  R  L  T  P  L  L  R  P  A  P  F  H  S
  525 CCCCCGGGCTGGGCTGGGGCTCCCGGTTCCGCGCCCCTGGCTACGGGGGTACGGCCCCCT
          P  P  G  W  A  G  A  P  G  S  A  P  L  A  T  G  V  R  P  P
  585 AGCCACCACTACTTGGGGCCTTCTGCTCAAGATCCCTCCAGGCACTGCGGATGGAGGCGT
          S  H  H  Y  L  G  P  S  A  Q  D  P  S  R  H  C  G  W  R  R
  645 GGGGGAGCCTTGGAACCTCAGACTAGTTTTGAATCCCTGCCCTGCCAGTCACTAGCTTGT
          G  G  A  L  E  P  Q  T  S  F  E  S  L  P  C  Q  S  L  A  C
  705 GGCTTTGAGTCTGACAAGATGTACCAGGTCCCATTGACACTGGACCGGGATGGGACCCTA
          G  F  E  S  D  K  M  Y  Q  V  P  L  T  L  D  R  D  G  T  L   (14)
  765 GTCCGGCTCCGCTTCACTATGGTGGCCCTGATCACGGTCTGCTGTCCACTTGTCGCCTTC
          V  R  L  R  F  T  M  V  A  L  I  T  V  C  C  P  L  V  A  F   (34)
  825 TTCTTCTGCATCCTGTGGTCCCTGCTCTTCCACTTCAAGGAGACAACATCTACACACTGT
          F  F  C  I  L  W  S  L  L  F  H  F  K  E  T  T  S  T  H  C   (54)
  885 GGGGTGCCCAATTACCTGCCATCAGTGAGCTCTGCCATTGGTGGGGAGGTTCCCCAGCGC
          G  C  P  N  Y  L  P  S  V  S  S  A  I  G  G  E  V  P  Q  R   (74)
  945 TACGTGTGGCGTTTCTGCATTGGCCTGCACTCGGCACCCCGCTTCTTGACAGCCTTCGCC
          Y  V  W  R  F  C  I  G  L  H  S  A  P  R  F  L  T  A  F  A   (94)
 1005 TATTGGAACCACTACCTCAGCTGTGCATCCCCGTGCCCGGGTTACCGCCTTCTCTGCCGC
          Y  W  N  H  Y  L  S  C  A  S  P  C  P  G  Y  R  L  L  C  R   (114)
 1065 CTACACTTCAGTCTCAATGTGGTGGAGAACCTGGCACTGCTCGTGCTCACCTATGTCTCC
          L  N  F  S  L  N  V  V  E  N  L  A  L  L  V  L  T  Y  V  S   (134)
 1125 TCCTCCGAGGACTTCACCATCCATGAAATGCTTTCATTGTGTTTATCGCGGCCTCCCTC
          S  S  E  D  F  T  I  H  E  N  A  F  I  V  F  I  A  A  S  L   (154)
 1185 AGTTACATGCTCCTCACCTGCATTCTCTGGCGGCTGACCAAGAAGCACACAGATCGCAAG
          S  Y  M  L  L  T  C  I  L  W  R  L  T  K  K  H  T  D  R  K   (174)
 1245 TCCTACAGCTGGAAACAACGGCTCTTCATCATCAACTTCATCTCCTTCTTCTCGGCGCTG
          S  Y  S  W  K  Q  R  L  F  I  I  N  F  I  S  F  F  S  A  L   (194)
 1305 GCTGTTTACTTCCGGCACAACATGTATTGTGAGGCTGGAGTGTACACCATCTTTGCCATC
          A  V  Y  F  R  H  N  M  Y  C  E  A  G  V  Y  T  I  F  A  I   (214)
 1365 CTGGAGTACACTGTGGTCCTAACCAACATGGCGTTCCACATGACAGCCTGGTGGGACTTC
          L  E  Y  T  V  V  L  T  N  M  A  F  H  M  T  A  W  W  D  F   (234)
 1425 GGGAACAAAGAGCTGCTAATAACCTCTCAGCCTGGGAAAAGAGATTCTAAACCCCGTCTC
          G  N  K  E  L  L  I  T  S  Q  P  G  K  R  D  S  K  P  R  L   (254)
 1485 TGATCCTGGAAAACAAGAAACCACTCTGGCCTTCCCTATCTCAGTGTCCTCTCTGGGCCC
          *
 1545 TTCTCCGTCTGGGGACTGGGAGAGAAGAGCAGGAAGGGTAGGACAAGGCTGACCCCAGCA
 1605 CTGCTGACTTCTCCCCCCCTCTCATCTCTCATGGGGGTCTTCAAGAAGCATCACTACTCA
 1665 CTGAAAGGTCCTAAAAAGCTGAGCTGGCAGGAAAGCCCTACCACTTGGTGCTAAGAAAAA
 1725 AAAAAAAAAAAAAAAAAAAAAAAAAAAAAAAAAAAAAAAAAAAAAAAAAAAAAAA
```

FIGURE 4

RAT FRAG1: TGG TCC CTG CTC TTC CA CCT CAA GG {AGA CAA CAT CTA CAC ACT GTG}
NEMATODE: TTA TCT CTT CTA CTG CA CTT TGA TC {AGG CAA CAT CTA CAC ATT GTG}
YEAST: TCT ACT GTT CAG CTG CA CAC CTG CA CAC GCA AC {ACC CTA CTA CAA CAC AAT GTC}

FIGURE 5

Comparison of FRAG1-Like Genes

```
FRAG1    MYQVPLTLDRGDTLVRLRFTMVALITVCCPLVAFFCILWSLLFHFKETTSTHCGVPNYL
T04A8.12 QRSADWMAFGDDDILSIPFKYFVICIGGLPSSALLICVILSLLLHFDQATSTHCEVANWL
SC108kD  ------------------------------------YSLHFHKIVTNAHYTYPDEWF

FRAG1    PSVSSAIGGEVPQRYVWRFCIGLHSAPRFLTAFAYWNHYLSCASPCPGYRLLCRLNFSLN
T04A8.12 PSISAAVSIYTPEKYIWRILIGLHIGPRLVVAIAFRNFLL------RFLCNLACFLN
SC108kD  PSVSATIGDRYPERSSIFQILIALTAFPRFLLLLG--HY------------FLVG

FRAG1    VVENLALLVLTYVSSSEDFTIHENAFIVFIAASLSYMLLTCILWRTLKKHIDRKSYSWKQ
T04A8.12 LLENFFLLALTSISSSEDHSLHAKCFGGFAICSIIYMLLSTWL-RRTATNLGGRSHEYKI
SC108kD  VLRTVSCGGWVYITSTDDHDIHDIFM------ITYIVLTLPWPIMITRYSSPLTSKNKG

FRAG1    RLFIINFISFFSALAVYFRHNMYCEAGVYTIFAILEYTVVLTNMAFHMTAWWDFGNKELL
T04A8.12 LGAAIFVLCFFLGAYLYWRHNTYCEPGIYTLFALVEYSAVLSNIFFHCTLYYDFHGKNIV
SC108kD  LTATIFFGTLFPMIYWYIQHSVQQRAGAYSIYAYFEWSLILLDIAFDAFAYADFKKIDIV

FRAG1    ITSQPGKRDSKPRL*
T04A8.12 LTSSFGGGHYNLLPT...
SC108kD  L...
```

FIGURE 6

```
..aacccgcc gttcgcgctc tgaccagccc gcagagccag cccccgaccc cgggccacct    60
gggcccccgg gttccgccgg cactctcgcc accaccgcgt gggtctgaca ag atg tac   118
                                                           Met Tyr
                                                             1 cag gtc cca cta cca ctg gat cgg gat ggg acc ctg gta cgg ctc cgc    166
Gln Val Pro Leu Pro Leu Asp Arg Asp Gly Thr Leu Val Arg Leu Arg
          5               10                  15 ttc acc atg gtg gcc ctg gtc acg gtc tgc tgt cca ctt gtc gcc ttc    214
Phe Thr Met Val Ala Leu Val Thr Val Cys Cys Pro Leu Val Ala Phe
         20              25                  30 ctc ttc tgc atc ctc tgg tcc ctg ctc ttc cac ttc aag gag aca acg    262
Leu Phe Cys Ile Leu Trp Ser Leu Leu Phe His Phe Lys Glu Thr Thr
 35              40                  45                  50 gcc aca cac tgt ggg gcc acg ccc tgc agg atg ttc tct gcg gcc tcc    310
Ala Thr His Cys Gly Ala Thr Pro Cys Arg Met Phe Ser Ala Ala Ser
                 55                  60                  65 cag cct ttg gac ccc gat ggg acc ttg ttc cgg ctt cgc ttc aca gcc    358
Gln Pro Leu Asp Pro Asp Gly Thr Leu Phe Arg Leu Arg Phe Thr Ala
             70                  75                  80 atg gtc tgg tgg gcc atc act ttt cct gtg ttc ggc ttc ttc ttc tgc    406
Met Val Trp Trp Ala Ile Thr Phe Pro Val Phe Gly Phe Phe Phe Cys
                 85                  90                  95 atc atc tgg tcc ctg gtg ttc cac ttt gag tac acg gtg gcc act gac    454
Ile Ile Trp Ser Leu Val Phe His Phe Glu Tyr Thr Val Ala Thr Asp
            100                 105                 110 tgt ggg gtg ccc aat tac ctg ccc tcg gtg agc tca gcc atc ggc ggg    502
Cys Gly Val Pro Asn Tyr Leu Pro Ser Val Ser Ser Ala Ile Gly Gly
115             120                 125                 130 gag gtg ccc cag cgc tac gtg tgg cgt ttc tgc atc ggc ctg cac tcg    550
Glu Val Pro Gln Arg Tyr Val Trp Arg Phe Cys Ile Gly Leu His Ser
                135                 140                 145 gcg cct cgc ttc ttg gtg gcc ttc gcc tac tgg aac cac tac ctc agc    598
Ala Pro Arg Phe Leu Val Ala Phe Ala Tyr Trp Asn His Tyr Leu Ser
            150                 155                 160 tgc acc tcc ccg tgt tcc tgc tat cgc ccg ctc tgc cgc ctc aac ttc    646
Cys Thr Ser Pro Cys Ser Cys Tyr Arg Pro Leu Cys Arg Leu Asn Phe
            165                 170                 175 ggc ctc aat gtc gtg gag aac ctc gcg ttg cta gtg ctc act tat gtc    694
Gly Leu Asn Val Val Glu Asn Leu Ala Leu Leu Val Leu Thr Tyr Val
            180                 185                 190 tcc tcc tcc gag gac ttc acc atc cac gaa aat gct ttc att gtg ttc    742
Ser Ser Ser Glu Asp Phe Thr Ile His Glu Asn Ala Phe Ile Val Phe
195             200                 205                 210
```

FIGURE 7A

```
att gcc tca tcc ctc ggg cac atg ctc ctc acc tgc att ctc tgg cgg     790
Ile Ala Ser Ser Leu Gly His Met Leu Leu Thr Cys Ile Leu Trp Arg
                215                 220                 225 ttg acc aag aag cac aca gta agt cag gag gat cgc aag tcc tac agc     838
Leu Thr Lys Lys His Thr Val Ser Gln Glu Asp Arg Lys Ser Tyr Ser
                230                 235                 240 tgg aaa cag cgg ctc ttc atc atc aac ttc atc tcc ttc ttc tcg gcg     886
Trp Lys Gln Arg Leu Phe Ile Ile Asn Phe Ile Ser Phe Phe Ser Ala
                245                 250                 255 ctg gct gtc tac ttt cgg cac aac atg tat tgt gag gct gga gtg tac     934
Leu Ala Val Tyr Phe Arg His Asn Met Tyr Cys Glu Ala Gly Val Tyr
                260                 265                 270 acc atc ttt gcc atc ctg gag tac act gtt gtc tta acc aac atg gcg     982
Thr Ile Phe Ala Ile Leu Glu Tyr Thr Val Val Leu Thr Asn Met Ala
275                 280                 285                 290 ttc cac atg acg gcc tgg tgg gac ttc ggg aac aag gag ctg ctc ata    1030
Phe His Met Thr Ala Trp Trp Asp Phe Gly Asn Lys Glu Leu Leu Ile
                295                 300                 305 acc tct cag cct gag gaa aag cga ttc tga acccttcagt cctgcttggg      1080
Thr Ser Gln Pro Glu Glu Lys Arg Phe
                310                 315 aggacgcagc ccactgccca gaaacaagaa acacgatacc attctggcct tccccacccc 1140
acatcctctc ttggccttac tgaagatggg ggaagggtaa gaaggaaggg tgtaggccaa 1200
ggctcacccc agtgctgctg gcttctcctc tccacccctc atatgggcgt ggggtcctca 1260
aacatcacct ttacctgaga ggccccaaga agctgagctg gcagagagct ccaccatttg 1320
gtgctaaaaa aaaaaacgtc ctgaggttca tgaccaccat ccagtttctg gcctttacac 1380
agtcaccttt cactgaggtc aggagcccct gagcagtggc tgctccctga caaccacagc 1440
catttctctg cacggggtc attcatagga ctaatgtatt tcatgatcta ctgtgcacat 1500
ccaggcctgt ggccacagtc ccctgctaaa gttgctcagg tgttctagtc ctgacttcac 1560 cttttttgatt tggtgtgtgc cctagggtat gtacccttcc ccatctgagc ctcggtgtgt 1620
ccatgtgtct ggcgggggat gggtggac                                    1648
```

FIGURE 7B

ID NOs. 5 and 11, respectively). According to another# FIBROBLAST GROWTH FACTOR RECEPTOR ACTIVATING GENE 1 AND RELATED COMPOSITIONS AND METHODS

CROSS-REFERENCE TO RELATED CASES

This application claims the benefit of U.S. Provisional Application No. 60/020,009, filed Jun. 18, 1996, which is incorporated herein by reference.

BACKGROUND OF THE INVENTION

This invention relates to a novel gene that activates Fibroblast Growth Factor Receptor 2 (FGFR2).

The fibroblast growth factors (FGFs) are a family of related proteins with roles in mitogenesis, differentiation, wound healing, and organogenesis (Basilico et al. *Adv. Cancer Res.* 59:115–165, 1992). The biological responses of FGFs are mediated through specific high-affinity receptor tyrosine kinases (Givol and Yayon, *FASEB J.* 6:3362–3369, 1992). Four distinct classes of fibroblast growth factor receptor (FGFR) that encode structurally related proteins have been identified: FGFR1/Flg, FGFR2/Bek, FGFR3, and FGFR4 (Diome et al., *EMBO J.* 9:2685–2692, 1990); Miki et al., *Science* 251:72–75, 1991; Keegan et al., *Proc. Natl. Acad. Sci. USA* 88:1095–1099, 1991; and Partanen et al., *EMBO J.* 10:1347–1354, 1992).

Activating mutations (i.e. mutations, leading to highly phosphorylated receptors, that are associated with various cancer states) in transmembrane domains of EGF receptor and FGFR3 were reported in rat leukemia and human achondroplasia, respectively (Ben-Levy et al., *J. Biol. Chem.* 267:17304–17313, 1992; and Shiang et al., *Cell,* 78:335–342, 1994). Furthermore, several growth factor receptors have been found to be activated by chromosomal rearrangement in cancer cells (Sawyers et al., *Cell* 77:171–173, 1994), including EGFR in leukemias, NGFR (TRK) in colon and thyroid carcinomas, HGFR (MET) in gastric carcinomas, RET in thyroid carcinomas, ALK in lymphomas, and PDGFRβ in myeloid leukemias.

One chromosomal rearrangement associated with chronic myelomonocytic leukemia was shown to create an expressed fusion between a novel gene sequence, tel, and the tyrosine kinase domain of the growth factor receptor PDGFRβ (Golub et al., *Cell* 77:307–316, 1994). tel appears to be a member of the ets gene family, members of which encode transcription factors. Genes other than growth factor receptors (GFRs), are activated and cause tumorigenesis by gene fusions resulting from chromosomal arrangement. For example, a majority of the cases of chronic myeloma leukemia (CML) contain a chromosornal rearrangement between chromosome 9 and 22 (t(9;22)(q34;q11) that results in a fusion of the oncogene α-abo, a cytoplasmic kinase, to bcr, which promotes myeloid tumorigenesis and is used as a diagnostic for the malignancy (Bernards et al., *Mol. Cell Biol.* 7:3231–3236, 1987; and Konopka et al., *Proc. Nat'l Acad. Sci.* 82:1810–1813, 1985).

SUMMARY OF THE INVENTION

We have cloned and sequenced rat and human FRAG1 cDNAs (SEQ ID NOs. 5 and 11, respectively). Chromosomal rearrangements resulting in a fusion of FRAG1 to fibroblast growth factor receptor 2 (FGFR2) causes a potent activation of FGFR2. Based on these discoveries, the present invention provides compositions and methods related to the isolated rat and human FRAG1 genes.

Accordingly, one embodiment of the invention is an isolated nucleic acid that comprises: (a) a sequence of at least 15 contiguous nucleotides of a native FRAG1 nucleic acid or the complement thereof; or (b) a sequence of at least 100 nucleotides having at least 70%, more preferably at least 80%, and yet more preferably at least 90%, and most preferably at least 95% nucleotide sequence similarity with a native FRAG1 nucleic acid (or a complement thereof), particularly with the rat or human FRAG1 nucleic acid (SEQ ID NOs. 5 and 11, respectively). According to another embodiment, the isolated nucleic acid encodes a polypeptide sequence having only silent or conservative substitutions to a native rat or human FRAG1 polypeptide. According to another embodiment, the isolated nucleic acid encodes a native or wild-type rat or human FRAG1 polypeptide (SEQ ID NOs. 6 and 12, respectively). According to another embodiment, the isolated nucleic acid encodes a polypeptide that, when expressed as an in-frame fusion with FGFR2, stimulates the transforming activity and autophosphorylation of FGFR2.

Another embodiment of the invention is a cell that comprises such FRAG1 nucleic acids, including expression vectors that are suitable for expression of recombinant FRAG1 polypeptides in a host cell. Such cells can be used to making FRAG1 polypeptides by culturing the cells under conditions suitable for expression of the FRAG 1 polypeptide, followed by isolation of the expressed FRAG1 polypeptide from the cell by conventional methods.

FRAG1 nucleic acids are useful for detecting an abnormality in a chromosome (e.g., a chromosomal rearrangement such as a fusion of FRAG1 to another gene that, when expressed, produces a fusion polypeptide) of a subject comprising the steps of: incubating chromosomes of a subject that comprises a chromosomal abnormality (e.g., a rearrangement resulting in a fusion of FRAG1 to another gene) with a FRAG1 nucleic acid probe or primer under conditions that cause the probe or primer to hybridize specifically with a native FRAG1 sequence. Hybridization of the probe or primer to the subject's chromosomes is compared with hybridization to a normal control chromosome, i.e., a chromosome known to lack the abnormality, thereby allowing the abnormality to be detected. Detection of chromosomal abnormalities can be accomplished, for example, by fluorescence in situ hybridization or nucleic acid amplification techniques. Such chromosome abnormalities may be diagnostic for disease states such as a neoplasia (e.g., an osteosarcoma).

Another embodiment of the invention is isolated FRAG1 polypeptides, e.g., polypeptides encoded by a FRAG1 nucleic acid as described above. For example, FRAG1 polypeptides according to various embodiments of the invention include polypeptides that comprise at least 10 consecutive amino acids of a native rat or human FRAG1 polypeptide; polypeptides having at least 70% amino acid sequence homology to a native rat or human FRAG1 polypeptide; and full-length native FRAG 1 polypeptides.

Another embodiment of the invention is an antibody that is specific for a native FRAG1 polypeptide.

FRAG1 genes can be isolated from species other than rat or human by contacting nucleic acids of the species with a FRAG1 probe or primer under at least moderately stringent nucleic acid hybridization conditions and isolating the FRAG1 gene to which the probe or primer hybridizes. For example, a cDNA or genomic library of the species can be screened with a FRAG1 probe, or primer, or mRNA or genomic DNA can be subjected to a nucleic acid amplification procedure to amplify a FRAG1 homolog of the species. In an alternative method of obtaining a FRAG1 gene of a species other than rat or human, an expression library comprising a plurality of cells that each express a recombinant polypeptide is contacted with a FRAG1-specific antibody under conditions that cause the FRAG1-specific antibody to specifically bind to a recombinant polypeptide encoded by a FRAG1 gene, thereby identifying a cell that expresses the FRAG1 gene. The FRAG1 gene can then be isolated from the cell that expresses the FRAG1 gene.

The foregoing and other aspects of the invention will become more apparent from the following detailed description and accompanying drawings.

BRIEF DESCRIPTION OF THE DRAWINGS

FIG. 2 shows the deduced C-terminal amino acid sequences (beginning at position 759) of FGFR2 cDNAs (FGFR2-WT, SEQ ID NO 1; FGFR2-ET, SEQ ID NO 2; FGFR2ROS, SEQ ID NO 3). The amino acid sequence and numbering of wild-type rat FGFR2 (rat FGFR2-WT SEQ ID NO. 1) is according to a three Ig-domain form of FGFR2-WT (Takagi et al., *J. Biol. Chem.* 269:23743–23749, 1994). The extended C-terminal domain of FGFR2-ROS (SEQ ID NO 3) is depicted by a series of dots. Numbers above the sequence denote the position of C-terminal tyrosine residues and asterisks represent termination codons.

FIG. 4 shows the nucleotide and predicted amino acid sequences of rat FRAG1 (SEQ ID NOs 5 and 6, respectively). The breakpoint in rat FRAG1 (between G and C, underlined) occurs 5' to the ATG (boxed) used for numbering the predicted amino acid sequence. The entire open reading frame was translated from the first amino acid sequence, but the amino acids are numbered (right) from the predicted start codon (boxed). A termination codon is marked by an asterisk.

FIG. 5 shows an alignment of the 5' ends of rat FRAG1 and corresponding sequences in a 30 kDa nematode gene (TO4A8.12) (SEQ ID NO 7) and a 107.9 kDa yeast protein (SC108kD) (SEQ ID NO 8). A particularly well-conserved region is bracketed.

FIG. 6 shows an alignment of the deduced polypeptide sequences of rat FRAG1(SEQ ID NO 6), T)4A8.12 (SEQ ID NO 9), and SC108 kD.

FIG. 7 shows a nucleotide sequence of a fill-length human FRAG1 cDNA (FRAG1-19) (SEQ ID NO 11) and the amino acid sequence thereof (SEQ ID NO 12).

DETAILED DESCRIPTION OF THE PREFERRED EMBODIMENTS

Figure 1:
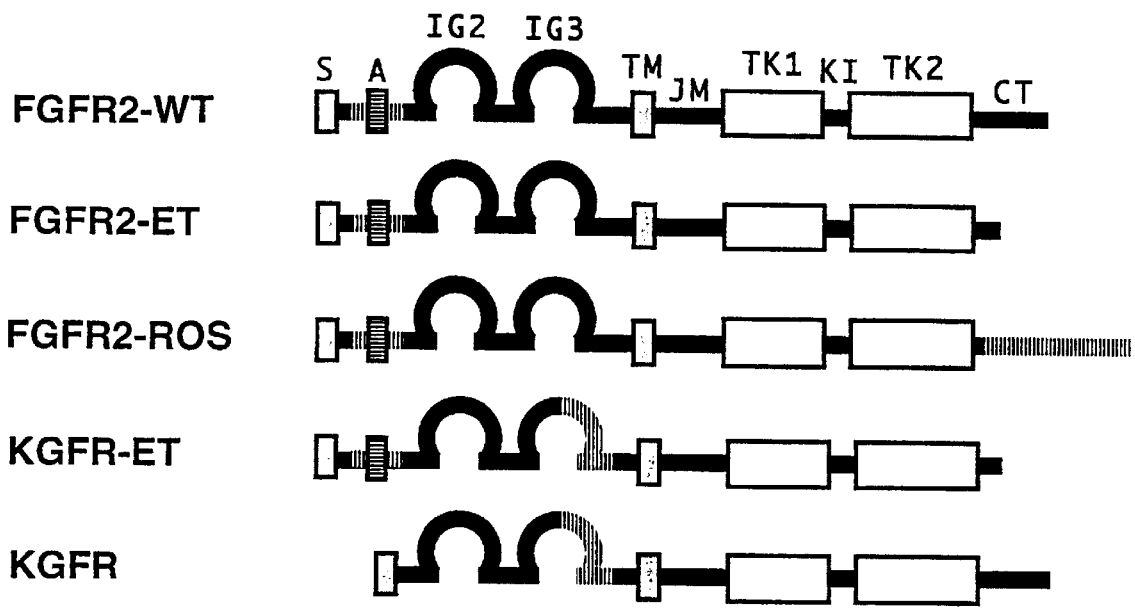
FIG. 1 is a schematic representation of FGFR2 isoforms and a C-terminal domain comparison of FGFR2-ROS with other FGFR2 cDNAs. The location of signal peptide (S), acidic (A), immunoglobulin-like (IG2, IG3), transmembrane (TM), juxtamembrane (JM), kinase insert (KI), tyrosine kinase (TK1, TK2) and carboxy-terminal (CT) regions are shown above the schematic. KGFR-type isoforms contain the sequence encoded by the K exon of the FGFR2/BEK gene in the second half of IG3 domain (shaded area). The variant C-terminal domain of FGFR2-ROS is indicated by a dashed box. All of these cDNAs are similar unless otherwise indicated and are inserted in a eukaryotic expression vector pCEV27 (Miki el al., *Gene* 83:137–146, 1989).

The present invention relates to a novel gene, FRAG1, which has been isolated from rat (see Lorenzi et al., *Proc. Natl. Acad. Sci. USA* 93:8956–8961, 1996, which is incorporated herein by reference) and human.

The rat FRAG1 cDNA was isolated as follows as a result of screening an osteosarcoma (ROS) cDNA library that was transformed into NIH 3T3 cells and transformants. One clone was shown to encode an isoform of FGFR2, FGFR2-ROS. It was determined that FGFR2-ROS was created by chromosomal rearrangement and included a C-terminal stretch of 313 amino acids originating from a novel gene, FRAG1. A probe derived from the FRAG1 portion of the FGFR2-ROS cDNA was used to isolate a gene that in rat encodes a protein of 254 amino acids long (SEQ ID NO 6).

The human FRAG1 cDNA was isolated by screening a library prepared from human fibroblast cells with a rat FRAG1 cDNA probe. Internal DNA sequence revealed that these cDNAs encoded the human homolog of rat FRAG1. The sequence of approximately 90% of the human FRAG1 cDNA has been determined (FIG. 7 and SEQ ID NO 10). A search of nucleotide sequence databases revealed that human FRAG1 is highly related to the rat FRAG1 sequence but contains unique regions not present in the rat FRAG1 sequence. The size of the human FRAG1 mRNA on Northern blots suggest that the human FRAG1-5CA clone is full length.

FGFR2-ROS was shown to be phosphorylated to a much greater extent than other FGFR2 isoforms and to be fully activated in a ligand-independent manner. The greater phosphorylation and highly activated state of FGFR2-ROS were shown to depend upon the C-terminal FRAG1 sequence. it was determined that FGFR2-ROS forms unusually stable dimers. Constitutive dimerization and autophosphorylation may underlie the potent transforming activity of FGFR2-ROS. It was also found that FRAG1 protein tends to accumulate in the Golgi complex. Thus, the altered subcellular localization of FGFR2-ROS could also explain its highly activated state.

FGFR2-FRAG1 fusions are a likely cause of osteosarcoma. Other disease states are known to involve chromosomal rearrangement. In particular, several growth factor receptors have been found to be activated by chromosomal rearrangement in cancer cells (Sawyers and Denny, *Cell* 77:171–173, 1994). Thus, the FRAG1 gene may be involved in other chromosomal rearrangements that are responsible for or associated with other disease states.

Definitions and Methods

The following definitions and methods are provided to better define the present invention and to guide those of ordinary skill in the art in the practice of the present invention. Unless otherwise noted, terms are to be understood according to conventional usage by those of ordinary skill in the relevant art. Definitions of common terms in molecular biology may also be found in Rieger et al., *Glossary of Genetics: Classical and Molecular*, 5th edition, Springer-Verlag: New York, 1991, and Lewin, *Genes V*, Oxford University Press: New York, 1994. The standard nomenclature for DNA bases (see 37 CPR §1.822) and the standard one- and three-letter nomenclature for amino acid residues are used.

Nucleic Acids

"FRAG1 Gene". The term "FRAG1 gene" or "FRAG1" refers to a native FRAG1-encoding nucleic acid or poly-nucleotide or a fragment thereof, e.g., the native FRAG1 cDNA or genomic sequences and alleles and homologs thereof. The term also encompasses variant forms of a native FRAG1 nucleic acid sequence or fragment thereof as discussed below, preferably a nucleic acid that encodes a polypeptide having FRAG1 biological activity. Native FRAG1 sequences include cDNA sequences and the corresponding genomic sequences (including flanking or internal sequences operably linked thereto, including regulatory elements and/or intron sequences).

Both double-stranded and single-stranded FRAG1 nucleic acids are encompassed. With reference to single-stranded forms of FRAG1 nucleic acids, "complementary nucleic acids" or "complements" (i.e., nucleic acids that base pair with such single-stranded forms) are also encompassed.

"Native". The term "native" refers to a naturally-occurring ("wild-type") nucleic acid or polypeptide, including, but not limited to, the native rat or human FRAG1 nucleic acid or the polypeptide encoded thereby.

"Homolot". A "homolog" of a FRAG1 gene is a gene sequence encoding a FRAG1 polypeptide isolated from a species other than a reference FRAG1 gene. For example, with reference to rat FRAG1, the human FRAG1 gene disclosed herein is a homolog. FRAG1 homologs from a variety of species other than rat and human can be readily obtained using probes and primers derived from rat and/or human FRAG1.

"Isolated". An "isolated" nucleic acid is one that has been substantially separated or purified away from other nucleic acid sequences in the cell of the organism in which the nucleic acid naturally occurs, i.e., other chromosomal and extrachromosomal DNA and RNA, by conventional nucleic acid-purification methods. The term also embraces recombinant nucleic acids and chemically synthesized nucleic acids.

Fragments, Probes. and Primers. A fragment of a FRAG1 nucleic acid is a portion of a FRAG1 nucleic acid that is less than full-length and comprises at least a minimum length capable of hybridizing specifically with a native FRAG1 nucleic acid under stringent hybridization conditions. The length of such a fragment is preferably at least 15 nucleotides, more preferably at least 20 nucleotides, yet more preferably at least 30 nucleotides, and most preferably at least 50 nucleotides of a native FRAG1 nucleic acid sequence.

Nucleic acid probes and primers can be prepared based on a native FRAG1 gene sequence. A "probe" is an isolated nucleic acid to which is attached a conventional detectable label or reporter molecule, e.g., a radioactive isotope, ligand, chemiluminescent agent, or enzyme. "Primers" are isolated nucleic acids that are annealed to a complementary target DNA strand by nucleic acid hybridization to form a hybrid between the primer and the target DNA strand, then extended along the target DNA strand by a polymerase, e.g., a DNA polymerase. Primer pairs can be used for amplification of a nucleic acid sequence, e.g., by the polymerase chain reaction (PCR) or other conventional nucleic-acid amplification methods.

Probes and primers are generally 15 nucleotides or more in length, preferably 20 nucleotides or more, more preferably 25 nueleotideg, and most preferably 10 nucleotides or more. Such probes and primers hybridize specifically to the FRAG1 sequence under high stringency hybridization conditions and hybridize specifically to a native FRAG1 sequence of another species under at least moderately stringent conditions. Preferably, probes and primers according to the present invention have complete sequence similarity with the native FRAG1 sequence, although probes differing from the FRAG1 sequence and that retain the ability to hybridize to native FRAG1 sequences may be designed by conventional methods.

Methods for preparing and using probes and primers are described, for example, in *Molecular Cloning: A laboratory Manual,* 2nd ed., vol. 1-3, ed. Sambrook et al., Cold Spring Harbor Laboratory Press, Cold Spring Harbor, N.Y., 1989 (hereinafter, "Sambrook et al., 1989"); *Current Protocols in Molecular Biology,* ed. Ausubel et al., Greene Publishing and Wiley-Interscience, N.Y., 1992 (with periodic updates) (hereinafter, "Ausubel et al., 1992); and Innis et al., *PCR Protocols: A Guide to Methods and Applications,* Academic Press: San Diego, 1990. PCR-primer pairs can be derived from a known sequence, for example, by using computer programs intended for that purpose such as Primer (Version 0.5, © 1991, Whitehead Institute for Biomedical Research, Cambridge, Mass.).

Primers and probes based on the native FRAG1 sequences disclosed herein can be used to confirm (and, if necessary, to correct) the disclosed rat and human FRAG1 sequences by conventional methods, e.g., by simply resequencing the deposited human FRAG1 cDNA or by recloning and sequencing a FRAG1 cDNA or genomic sequence by conventional methods.

Substantial Similarity. A first nucleic acid is "substantially similar" to a second nucleic acid if, when optimally aligned (with appropriate nucleotide insertions or deletions) with the other nucleic acid (or its complementary strand), there is at least about 70% nucleotide sequence identity, preferably at least about 80% identity, and most preferably at least about 90% identity. Sequence similarity can be determined by comparing the nucleotide sequences of two nucleic acids using sequence analysis software such as the Sequence Analysis Software Package of the Genetics Computer Group, University of Wisconsin Biotechnology Center, Madison, Wis.

Alternatively, two nucleic acids are substantially similar if they hybridize under stringent conditions, as defined below.

"Operably Linked". A first nucleic-acid sequence is "operably" linked with a second nucleic-acid sequence when the first nucleic-acid sequence is placed in a functional relationship with the second nucleic-acid sequence. For instance, a promoter is operably linked to a coding sequence if the promoter affects the transcription or expression of the coding sequence. Generally, operably linked DNA sequences are contiguous and, where necessary to join two protein coding regions, in reading frame.

"Recombinant". A "recombinant" nucleic acid is made by an artificial combination of two otherwise separated segments of sequence, e.g., by chemical synthesis or by the manipulation of isolated segments of nucleic acids by genetic engineering techniques.

Techniques for nucleic-acid manipulation are well-known (see, e.g., Sambrook et al., 1989, and Ausubel et al., 1992). Methods for chemical synthesis of nucleic acids are discussed, for example, in Beaucage and Carruthers, *Tetra. Letts.* 22 1859–1862, 1981, and Matteucei et al., *J. Am. Chem. Soc.* 103:3185, 1981. Chemical synthesis of nucleic acids can be performed, for example, on commercial automated oligonucleotide synthesizers.

Vectors, Transformation, Host cells. Natural or synthetic nucleic acids according to the present invention can be incorporated into recombinant nucleic-acid constructs or vectors that can be introduced into and replicated in a host cell. Such vectors include selectable or screenable marker genes, well-known sequences that allow the vector to be replicated in a given prokaryotic or eukaryotic host cell (e.g., origin of replication), transcriptional and translational control sequences that are functional in the host cell (e.g., promoters, enhancers), secretion signals, etc. Compositions and methods for preparing and using vectors and host cells, including host cell transformation, are discussed, inter alia, in Sambrook, 1989, or Ausubel, 1994. Mammalian or other eukaryotic host cells, such as those of yeast, filamentous fungi, plant, insect, amphibian or avian species, are useful for production of the proteins of the present invention by conventional methods.

A cell, tissue, organ, or organism into which a foreign nucleic acid, such as a recombinant vector, has been introduced is considered "transformed", "transfected", or "transgenic."

Nucleic acid constructs can be introduced into a host cell by any suitable conventional method, including electroporation; transfection employing calcium chloride, rubidium chloride calcium phosphate, DEAE-dextran, or other substances; microprojectile bombardment; lipofection; infection (where the vector is an infectious agent, such as a retroviral genome); etc. See, e.g., Sambrook, 1989, and Ausubel, 1994.

Nucleic-Acid Hybridization; "Stringent Conditions"; "Specific". The nucleic-acid probes and primers of the present invention hybridize under stringent conditions to a target DNA sequence, e.g., to a FRAG1 gene.

The term "stringent conditions" is functionally defined with regard to the hybridization of a nucleic-acid probe to a target nucleic acid (i.e., to a particular nucleic-acid sequence of interest) by the specific hybridization procedure discussed in Sambrook et al., 1989, at 9.52–9.55. See also, Sambrook et al., 1989 at 9.47–9.52, 9.56–9.58; Kanehisa, *Nucl. Acids Res.* 12:203–213, 1984; and Wetmur and Davidson, *J. Mol. Biol.* 31:349–370, 1968. "Moderate stringency" hybridization conditions are defined as hybridization at 60° C. in a hybridization solution including 6×SSC, 5×Denhardt's reagent, 0.5% SDS, 100 μg/mL denatured, fragmented salmon sperm DNA, and a labeled probe (Sambrook, 1989), and "high stringency" conditions are hybridization at 65° C., or preferably at 68° C., in the same hybridization solution.

Regarding the amplification of a target nucleic-acid sequence (e.g. by PCR) using a particular amplification primer pair, "high stringency conditions" are conditions that permit the primer pair to hybridize only to the target nucleic-acid sequence to which a primer having the corresponding wild-type sequence (or its complement) would bind and preferably to produce a unique amplification product.

The term "specific for (a target sequence)" indicates that a probe or primer hybridizes under given hybridization conditions only to the target sequence in a sample comprising the target sequence.

Nucleic-Acid Amplification. As used herein, "amplified DNA" refers to the product of nucleic-acid amplification of a target nucleic-acid sequence. Nucleic-acid amplification can be accomplished by any of the various nucleic-acid amplification methods known in the art, including the polymerase chain reaction (PCR). A variety of amplification methods are known in the art and are described, inter alia, in U.S. Pat. Nos. 4,683,195 and 4,683,202 and in *PCR Protocols: A Guide to Methods and Applications*, ed. Innis et al., Academic Press, San Diego, 1990.

Nucleotide-Sequence Variants of Native FRAG1 Nucleic Acids and Amino Acid Seguence Variants of Native FRAG1 Proteins. Using the nucleotide and the amino-acid sequence of the FRAG1 polypeptides disclosed herein, those skilled in the art can create DNA molecules and polypeptides that have minor variations in their nucleotide or amino acid sequence.

"Variant" DNA molecules are DNA molecules containing minor changes in a native FRAG1 sequence, i.e., changes in which one or more nucleotides of a native FRAG1 sequence is deleted, added, and/or substituted, preferably while substantially maintaining a FRAG1 biological activity. Variant DNA molecules can be produced, for example, by standard DNA mutagenesis techniques or by chemically synthesizing the variant DNA molecule or a portion thereof. Such variants preferably do not change the reading frame of the protein-coding region of the nucleic acid and preferably encode a protein having no change, only a minor reduction, or an increase in FRAG1 biological function.

Amino-acid substitutions are preferably substitutions of single amino-acid residues. DNA insertions are preferably of about 1 to 10 contiguous nucleotides and deletions are preferably of about 1 to 30 contiguous nucleotides. Insertions and deletions are preferably insertions or deletions from an end of the protein-coding or non-coding sequence and are preferably made in adjacent base pairs. Substitutions, deletions, insertions or any combination thereof can be combined to arrive at a final construct.

Preferably, variant nucleic acids according to the present invention are "silent" or "conservative" variants. "Silent" variants are variants of a native FRAG1 sequence or a homolog thereof in which there has been a substitution of one or more base pairs but no change in the amino-acid sequence of the polypeptide encoded by the sequence. "Conservative" variants are variants of the native FRAG1 sequence or a homolog thereof in which at least one codon in the protein-coding region of the gene has been changed, resulting in a conservative change in one or more amino acid residues of the polypeptide encoded by the nucleic-acid sequence, i.e., an amino acid substitution. A number of conservative amino acid substitutions are listed below. In addition, one or more codons encoding cysteine residues can be substituted for, resulting in a loss of a cysteine residue and affecting disulfide linkages in the FRAG1 polypeptide.

Substantial changes in function are made by selecting substitutions that are less conservative than those listed in Table 1, e.g., causing changes in: (a) the structure of the polypeptide backbone in the area of the substitution; (b) the charge or hydrophobicity of the polypeptide at the target site; or (c) the bulk of an amino acid side chain. Substitutions generally expected to produce the greatest changes in protein properties are those in which: (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine.

TABLE 1

Conservative Amino Acid Substitutions

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |

TABLE 1-continued

Conservative Amino Acid Substitutions

| Original Residue | Conservative Substitutions |
|---|---|
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| val | Ile, Leu |

Deposit Information. The human FRAG1 cDNA has been deposited with the American Type Culture Collection (ATCC), 12301 Parklawn Drive, Rockville, Md., 20852, U.S.A. under the terms of the Budapest Treaty on Jun. 9, 1997 (ATCC NO 209102).

Polypeptides

"FRAG1 Protein". The term "FRAG1 protein" (or polypeptide) refers to a protein encoded by a FRAG1 nucleic acid, including alleles, homologs, and variants of a native FRAG1 nucleic acid, for example. A FRAG1 polypeptide can be produced by the expression of a recombinant FRAG1 nucleic acid or be chemically synthesized. Techniques for chemical synthesis of polypeptides are described, for example, in Merrifield, *J. Amer. Chem. Soc.* 85:2149–2156, 1963.

Polypeptide Sequence Homology. Ordinarily, FRAG1 polypeptides encompassed by the present invention are at least about 70% homologous to a native FRAG1 polypeptide, preferably at least about 80% homologous, and more preferably at least about 95% homologous. Such homology is considered to be "substantial homology," although more important than shared amino-acid sequence homology can be the common possession of characteristic structural features and the retention of FRAG1 biological activity.

Polypeptide homology can be analyzed by any conventional method, e.g., by using sequence analysis software such as the Sequence Analysis Software Package of the Genetics Computer Group, University of Wisconsin Biotechnology Center, Madison, Wis.) or other well-known software.

"Isolated," "Purified," "Homogeneous." A polypeptide is "isolated" if it has been separated from the cellular components (nucleic acids, lipids, carbohydrates, and other polypeptides) that naturally accompany it. Such a polypeptide can also be referred to as "pure" or "homogeneous" or "substantially" pure or homogeneous. Thus, a polypeptide which is chemically synthesized or recombinant (i.e., the product of the expression of a recombinant nucleic acid, even if expressed in a homologous cell type) is considered to be isolated. A monomeric polypeptide is isolated when at least 60% by weight of a sample is composed of the polypeptide, preferably 90% or more, more preferably 95% or more, and most preferably more than 99%. Protein purity or homogeneity is indicated, for example, by polyacrylamide gel electrophoresis of a protein sample, followed by visualization of a single polypeptide band upon staining the polyacrylamide gel; high pressure liquid chromatography; or other conventional methods.

Protein Purification. The polypeptides of the present invention can be purified by any of the means known in the art. Various methods of protein purification are described, e.g., in *Guide to Protein Purification*, ed. Deutscher, *Meth. Enymol.* 185, Academic Press, San Diego, 1990; and Scopes, *Protein Purification: Principles and Practice*, Springer Verlag, New York, 1982.

Variant and Modified Forms of FRAG1 Polypeptides. Encompassed by the FRAG1 polypeptides of the present invention are variant polypeptides in which there have been substitutions, deletions, insertions or other modifications of a native FRAG1 polypeptide. The variants substantially retain structural characteristics and biological activities of a corresponding native FRAG1 polypeptide and are preferably silent or conservative substitutions of one or a small number of contiguous amino acid residues.

A native FRAG1 polypeptide sequence can be modified by conventional methods, e.g., by acetylation, carboxylation, phosphorylation, glycosylation, ubiquitination, and labeling, whether accomplished by in vivo or in vitro enzymatic treatment of a FRAG1 polypeptide or by the synthesis of a FRAG1 polypeptide using modified amino acids.

Labeling. There are a variety of conventional methods and reagents for labeling polypeptides and fragments thereof. Typical labels include radioactive isotopes, ligands or ligand receptors, fluorophores, chemniluminescent agents, and enzymes. Methods for labeling and guidance in the choice of labels appropriate for various purposes are discussed, e.g., in Sambrook et al., 1989 and Ausubel et al., 1992.

Polypeptide Fragments. The present invention also encompasses fragments of a FRAG1 polypeptide that lack at least one residue of a native full-length FRAG1 polypeptide. Preferably, such a fragment retains FRAG1 biological activity or possesses a characteristic functional domain or an immunological determinant characteristic of a native FRAG1 polypeptide. Immunologically active fragments typically have a minimum size of 7 to 17 or more amino acids. Preferred embodiments of the polypeptides of the invention include at least 10, more preferably at least 15, yet more preferably at least 20, and most preferably at least 25 consecutive amino acids of a native FRAG1 polypeptide.

The terms "biological activity", "biologically active", "activity" and "active" refer primarily to the characteristic biological activity or activities of a native FRAG1 polypeptide, including, but not limited to, the ability to stimulate the transforming activity and autophosphorylation of FGFR2 when fused thereto, as described in greater detail in Example 1.

Fusion Polypeptides. The present invention also provides fusion polypeptides including, for example, heterologous fusion polypeptides in which a FRAG1 polypeptide sequence is joined to a fusion partner. Such fusion polypeptides can exhibit biological properties (such as substrate or ligand binding, enzymatic activity, antigenic determinants, etc.) derived from each of the fused sequences. Fusion polypeptides are preferably made by the expression of recombinant nucleic acids produced by standard techniques. Fusion of FRAG1 to FGFR2 has been found to potently activate FGFR2. It is expected that fusion of FRAG1 to other growth factors, among other protein fusion partners, also will stimulate transforming activity and/or autophosphorylation of the fusion partner.

Polypeptide Sequence Determination. The sequence of a polypeptide of the present invention can be determined by any of various methods known in the art.

Antibodies

The present invention also encompasses polyclonal and/or monoclonal antibodies capable of specifically binding to a FRAG1 polypeptide and/or fragments thereof. Such antibodies are raised against a FRAG1 polypeptide or fragment thereof and are capable of distinguishing a FRAG1 polypeptide from other polypeptides, i.e., are "FRAG1-specific." Encompassed by the present invention are double- and single-chain FRAG1-binding antibody fragments (e.g., Fv, Fab, (Fab')$_2$, etc.), chimeric antibodies, humanized antibodies, and other modified antibodies made by conventional methods. Conventional methods are used for the preparation and use of antibodies according to the present invention, including various immunoassay techniques and applications, see, e.g., *Goding, Monoclonal Antibodies: Principles and Practice,* 2d ed, Academic Press, New York, 1986; and Harlow and Lane, *Antibodies: A Laboratory Manual,* Cold Spring Harbor Laboratory, Cold Spring Harbor, N.Y., 1988. FRAG1-specific antibodies are useful, for example in: purifying a FRAG1 polypeptide from a biological sample, such as a host cell expressing recombinant a FRAG1 polypeptide; in cloning a FRAG1 allele or homolog from an expression library; as antibody probes for protein blots and immunoassays; etc.

Anti-FRAG1 antibodies can be labeled by any of a variety of conventional methods. Suitable labels include, but are not limited to, radionuclides, enzymes, substrates, cofactors, inhibitors, fluorescent agents, chemiluminescent agents, magnetic particles, etc.

Uses of Rat and Human FRAG1 Nucleic Acids and Polypeptides

Obtaining Alleles and Homologs of Rat or Human FRAG1. Alleles and homologs of rat and human FRAG1 can readily be obtained from other species using probes and primers derived from the sequences disclosed herein by conventional methods, e.g., by screening a cDNA or genomic library with a probe that specifically hybridizes to a native FRAG1 sequence under at least moderately stringent conditions (e.g., to the rat FRAG1 cDNA or a fragment thereof), by PCR or another amplification method using a primer or primers that specifically hybridize to a native FRAG1 sequence under at least moderately stringent conditions, or by identification of FRAG1 alleles or homologs in an expression library using FRAG1-specific antibodies.

Probes and primers based on the rat FRAG1 sequence disclosed herein can also be used to obtain genes having substantial sequence homology with rat FRAG1 but different biological activity.

Diagnostics. Most tumor types undergo chromosomal rearrangements that may be consistently associated with and diagnostic of particular tumor types. The sites of these rearrangements often map to genes that are thought to be critically involved in tumor progression. For example, several genes involved in cellular growth control are known to undergo rearrangement with other genes in tumor cells. In chronic myelomonocytic leukemia (CMML), a chromosomal rearrangement between the genes encoding platelet-derived growth factor receptor (PDGFR) and tel results in the expression of a PDGFR-tel fusion protein in the tumor cells and is diagnostic for CML. Several receptor tyrosine kinase receptors undergo structural alterations or are over-expressed in human cancer. In the case of Tpr, an unknown gene, chromosomal rearrangements at the Tpr locus frequently occur with multiple receptors, thereby converting silent receptors into potent oncogenes.

We have isolated a constitutively active form of FGFR2 from cells derived from an osteosarcoma that is activated by chromosomal rearrangement with FRAG1. The FGFR2 gene has been shown to be involved in cancers of the stomach and in diseases of bone malformation. Many other growth factor receptors, including FGFR1, FGFR3, EGFR, erbB2, and erbB3 have been implicated in human disease. FRAG1 rearrangements with the genes encoding these receptors may be utilized as a marker for cancers such as osteosarcoma, for example, and other disease states. Such rearrangements may be detected by using FRAG1-derived primers for nucleic acid amplification (e.g., PCR) or FRAG1-derived probes for fluorescence in situ hybridization (FISH), for example.

Fluorescence in situ hybridization (FISH), for example, is one useful technique for identifying and characterizing chromosomal abnormalities by staining specific chromosomes in a manner that allows numerical and structural aberrations to be easily evaluated in either metaphase or interphase cells (Pinkel et al., *Proc. Natl. Acad. Sci. USA* 85:9138–9142, 1988). The characterization of cytogenetic aberrations in tumors has contributed to the understanding of carcinogenesis, tumor progression, and to clinical management decisions. A "marker chromosome" is a chromosome differing from a normal chromosome, for example, in size and/or banding pattern, that is characteristic of the cells in a particular tumor or other disease state and is not found in normal cells. Such marker chromosomes frequently result from the rearrangement and recombination of portions of a normal chromosome or several normal chromosomes. The availability of rat and human FRAG1 genes is permits the identification of marker chromosomes that are diagnostic for osteosarcoma and other disease states, particularly neoplasias.

Therapeutic uses. Agents capable of inhibiting FRAG1 activity, such as FRAG1-specific antibodies, FRAG1-derived antisense or triplex helix-forming nucleic acids, or other agents, are useful for treating diseases involving FRAG1 rearrangements by blocking FRAG1-mediated activation of receptors.

Drug Screening. FRAG1 polypeptides are useful for screening compounds by conventional drug-screening methodologies. For example, compounds that bind to FRAG1 polypeptides can be identified by any of various well-known competitive binding assays, including methods for screening combinatorial libraries in which large numbers of different peptides are synthesized on a solid substrate or presented by a recombinant expression as part of a phage protein (e.g., a coat protein of a filamentous phage), for example. The peptide test compounds are reacted with a FRAG1 polypeptide and washed. Bound FRAG1 polypeptide is then detected to determine the location of the bound peptide, the sequence of which can be determined readily.

The invention will be better understood by reference to the following Examples, which are intended to merely illustrate the best mode now known for practicing the invention. The scope of the invention is not to be considered limited thereto.

EXAMPLES

Example 1

Cloning and Analysis of Rat FRAG1

Materials and Methods

FGFR2 expression constructs and transformants. FGFR2-WT was engineered by replacing the variant carboxyl-terminal domain of p822 with the normal C-terminus of the KGFR at the BglII site (amino acid position 696). The coding regions of mouse and rat KGFR are identical in this region. A termination codon was inserted by PCR to introduce a deletion in the C-terminus of FGFR2-WT at position 764 to generate Δ764-. Expression constructs were transfected into NIH 3T3 fibroblasts by calcium-phosphate precipitation (Wigler er al., *Cell* 14:725–731, 1978). Mass cultures of NIH 3T3 cells expressing the recombinant proteins were obtained by selection with G418 (750 μg/ml).

Protein Analysis. Immunoprecipitation and immunoblot analysis using IgG-purified rabbit polyclonal antiserum generated against the amino acids 476–822 of the cytoplasmic domain of FGFR2 (αFGFR2, 1:1000) or anti-phosphotyrosine monoclonal antibody (αPTYR, 1:1000, Upstate Biotechnology, Inc.) was conducted as described (Miki et al., *Science* 251:72–75, 1991). For covalent crosslinking experiments, cells were incubated in 0.3 mM disuccinimidyl suberate dissolved in dimethylsulfoxide (DMSO) or DMSO alone for 20 minutes at 4° C. The crosslinking reaction was terminated by addition of 10 mM Tris-HCl (pH 7.5), 200 mM glycine, 2 mM EDTA, and lysate were prepared and analyzed as described above.

Immunofluorescent staining. pCEV29F3, an expression vector encoding three tandem copies of the FLAG nonapeptide was engineered by a modification of pCEV27. Triple FLAG epitope-tagged rat FRAG1 (F3-FRAG1) was generated by inserting rat FRAG1 cDNA (encoding amino acids 1–244) into pCEV29F3 in frame with the triple FLAG epitope. NIH 3T3 transfectants of F3-FRAG1 or pCEV29F3 were subjected to immunofluorescence staining using an anti-FLAG monoclonal antibody (1:200, IBI) as described (Jackman et al., *EMBO J.* 14:1646–1654, 1995). Bound antibody was visualized using a lissamine rhodamine (LRSC)-conjugated goat anti-mouse antisera (1:200, Jackson Laboratories, Bar Harbor, Me.).

Results

Expression cloning of a transforming FGFR2 from osteosarcoma cells. A novel oncogene, ost, was previously isolated from ROS 17/2.8 cells using an expression cloning system (Miki et al., *Nature* 362:462–465, 1993). However, the ost oncogene showed no evidence of rearrangement in ROS cells, indicating that it was not responsible for osteosarcoma formation. Several more plasmids with transforming activity were rescued from the foci induced by the ROS cell expression cDNA library. Sequence analysis of the 5'-end of the cDNA inserts revealed that one of these plasmids, p822, encodes a fibroblast growth factor, FGFR2. p822 showed high-titered transforming activity [>10⁴ focus forming units (ffu)/pmol DNA] following transfection into NIH 3T3 cells. The FGFR2/BEK gene encodes two receptor species, FGFR2 and KGFR, with respect to ligand-binding specificity (FIG. 1).

It was previously shown that KGFR transforms NIH 3T3 cells by creation of an autocrine loop whereas FGFR2 does not. KGF, unlike FGFR2, is secreted from NIH 3T3 cells and binds and activates KGFR (Miki et al., *Science* 251:72–75, 1991). However, sequence analysis of the extracellular domain of the receptor revealed that it contained the third Ig domain sequence of FGFR2. Other regions of the extracellular domain were completely identical to the previously reported rat KGFR (Takagi en al., *J. Biol. Chem.* 269:23743–23749, 1994). Activating mutations in transmembrane domains of EGF receptor and FGFR3 were reported in rat leukemia and human achondroplasia, respectively (Ben-Levy, *J. Biol. Chem.* 267:17304–17313, 1992). However, the transmembrane domain of FGFR2 from ROS cells is also identical to rat KGFR, indicating that neither the extracellular or transmembrane domain of FGFR2 from ROS cells contains sequences that are known to activate the receptor function. Therefore, we reasoned that the FGFR2 from ROS cells, designated FGFR2-ROS, has been activated by an unknown mechanism and further examined the structure and function of the receptor.

FGFR2-ROS contains an altered C-terminus. Sequence analysis of the entire FGFR2-ROS cDNA predicted an isoform of FGFR2 with two Ig domains and an acidic region (FIG. 1). Comparison of FGFR2-ROS with mouse KGFR and FGFR2 showed that it encodes an FGFR2 variant that diverges from FGFR2 at amino acid 763. Following amino acid 763, FGFR2-ROS contains a unique 313 amino-acid stretch at its C-terminus (FIG. 1). No-matches were observed when protein data bases were searched for homology to known sequences with the unique C-terminal region of FGFR2-ROS. In addition, the nucleotide sequence encoding the unique C-terminus and 290 bp of flanking 3'-untranslated sequence of the FGFR2-ROS cDNA revealed little identity to any known DNA sequences, suggesting that the 3' portion of FGFR2-ROS cDNA is derived from an unknown gene.

FGFR2-ROS is fully activated in a ligand-independent manner. To examine the regulatory effect of the C-terminal domain, we utilized a natural isoform of mouse KGFR, KGFR-ET (ET refers to "early termination"), that contained a partially truncated C-terminus that is identical to the C-terminus of the human FGFR2 isoform, TK25 (Champion-Arnaud et al., *Oncogene* 6:979–987, 1991). To avoid receptor activation by KGF secreted from NIH 3T3 cells, the extracellular domain of KGFR and KGFR-ET was replaced with the extracellular domain of FGFR2-ROS, thereby generating FGFR2-WT and FGFR2-ET, respectively (FIG. 1). A comparison of the C-terminal sequences of FGFR2-WT (SEQ ID NO 1), FGFR2-ROS (SEQ ID NO 3) and FGFR2-ET (SEQ ID NO 2) is shown in FIG. 2.

FGFR2-WT, FGFR2-ET and FGFR2-ROS were compared for their ability to morphologically transform NIH 3T3 cells. Only FGFR2-ROS exhibited high-titer transforming activity (Table 2). The activity was even higher than that of KGFR, which can be bound and activated by KGF secreted from the host cells. Lack of significant transforming activity in FGFR2-WT indicates that the ligand-binding domain of FGFR2-ROS is functional and can suppress the catalytic domain of the normal receptor, since the FGFR2-WT clone is a chimera of the ligand-binding domain of FGFR2-ROS and the cytoplasmic domain of KGFR (FIG. 1). Therefore, FGFR2-ROS appeared to have been maximally activated in a ligand-independent manner. On the other hand, FGFR2-ET, an FGFR2 isoform with a different C-terminal alteration, was weakly transforming (Table 2). The foci induced by FGFR2-ET transfection were less aggressive than those of FGFR2-ROS and could not be identified within 10 days after transfection, whereas FGFR2-ROS-induced foci were much more aggressive and were clearly detectable earlier in the course of the transfection. In contract, FGFR2-WT did not show significant transforming activity even at this later stage. These data suggest that partial deletion or replacement of the C-terminus of the FGFR2 can mediate ligand independent activation.

Growth in semi-solid medium of NIH 3T3 transfectants expressing these receptor was also examined. Transfectants containing only vector or FGFR2-WT did not grow efficiently, whereas FGFR2-ET and KGFR showed modest cloning efficiency (Table 2). In contrast, FGFR2-ROS showed markedly higher efficiency in this assay, indicating the highly activated state of this receptor. Nonetheless, all of the NIH 3T3 cells transfected with FGFR2 expression vectors induced tumors efficiently when these transfectants were injected into athymic nude mice. This result suggests that overproduction of FGFR2 generated tumors under these conditions, since the ligands of FGFR2, such as αFGF, may be available for receptor activation in nude mice.

TABLE 2

Oncogenic Activity of FGFR2 Variants

| DNA | Transforming Activity* | Cloning efficiency† | Tumorigenicity‡ |
|---|---|---|---|
| pCEV27 | <1 × 10$^0$ | 0.2 | 0/6 |
| KGFR | 1.4 × 10$^4$ | 2.7 | 6/6 |
| FGFR2-WT | <1 × 10$^0$ | .03 | 6/6 |
| FGFR2-ET | 8.0 × 10$^2$ | 1.8 | 6/6 |
| FGFR2-ROS | 2.6 × 10$^4$ | 20.5 | 6/6 |

* NIH 3T3 fibroblasts were transfected with serial dilutions of the indicated plasmid DNAs plus 40 μg of calf thymus DNA as carrier. The number of foci produced by each DNA were counted after three weeks and transformed activity was expressed as the number of ffu per pmol DNA (ffu/pmol, n = 4).
†To estimate cloning efficiency, G418-selected transfectants were suspended in 0.4% soft agar in the presence of DMEM containing 10% calf serum and the number of colonies were counted after 23 days in culture.
‡1 × 10$^5$ or 1 × 10$^6$ NIH 3T3 cells transfected with the indicated plasmids were injected subcutaneously into athymic mice and tumors were scored 18 days following injection.

The altered C-terminal tail of FGFR2-ROS is required for full activation. Comparison of the C-terminal of FGFR2-ET and FGFR2-ROS with that of FGFR2-WT (SEQ ID NOS 2, 3 and 1 respectively) suggested that the loss of the C-terminal domain may be responsible for the higher transforming activity of the variant FGFRs. To examine if the C-terminal tail of FGFR2-ROS has an important role in receptor activation, this sequence was deleted from FGFR2-ROS to generate FGFR2Δ764-. The transforming activities of Δ764 and FGFR2-ROS were then compared after transfection of NIH 3T3 cells. Whereas FGFR2-ROS exhibited a high transforming activity even at an early stage (2.6×10$^4$ ffu/pmol DNA), Δ764- did not show significant transforming activity. However, Δ764- showed weaker transforming activity (5.0×10$^2$ ffu/pmol DNA) at a later stage. FGFR2-ROS was 50-fold more active than Δ764- at this later stage. These results strongly indicate that the C-terminal sequence of FGFR2-ROS plays a major role in the activation of this receptor variant.

PGFR2-ROS is highly phosphorylated in NIH 3T3 transfectants. To assess the effects of different C-terminal sequences on receptor phosphorylation, FGFR2 was immunoprecipitated from soluble lysates (2 mg) of pCEV27- or FGFR2-NIH 373 transfectants with an affinity purified anti-FGFR2 antiserum (αFGFR2). Immunoprecipitated FGFR2 was then analyzed for phosphorylation levels by SDS-polyacrylamide gel electrophoresis (PAGE, 8%), transfer of the immunoprecipitated proteins to Immobilon-P, and blotting with either an anti-phosphotyrosine antibody (αPTYR) or αFGFR2). The wild-type receptor displayed a low level of receptor phosphorylation, whereas phosphorylation of FGFR2-ET and Δ764- proteins was detectable only after a longer exposure of the autoradiogram. In contrast, FGFR2-ROS was identified as a broad band of greater than 300 kDa and phosphorylated at a similar level as KGFR, which was activated by KGF secreted from the transfectants. A minor band (180 kDa) of FGFR2-ROS was barely detectable with αFGPR antibody but readily detectable with αPTYR, indicating that this minor band was also highly phosphorylated. Immunoblot analysis of the same immunoprecipitates with αFGFR2 antibody revealed that the expression levels of different FGFR2 constructs in the NIH 3T3 transfectants were comparable. FGFR2-WT, FGFR2-ET and Δ764- were identified as broad bands of approximately 160 kDa as well as lesser abundant 110 kDa, 100 kDa and 90 kDa bands, respectively. The receptor in the KGFR transfectant was identified as 110 kDa and 95 kDa forms. The larger broad bands observed in these transfectants probably represent receptor species modified by post-transnational modifications of the extracellular domains by glycosaminoglycans, since treatment with enzymes that specifically degrade glycosaminoglycans reduced the size of these receptors to lower molecular weight forms that roughly correspond to their predicted molecular sizes.

FGFR2-ROS appears to form unusually stable dimers. The cDNA encoding FGFR2-ROS predicts a protein with a molecular mass of 110 kDa. However, >300 kDa and 180 kDa species were observed as the predolminant and minor forms of the receptor in FGFR2-ROS transfectants, respectively. To further analyze the FGFR2 variants, NIH 3T3 cells expressing the indicated constructs were incubated in the presence (+) or absence (−) of disuccinimidyl suberate for 20 minutes at 4° C., lysed, and immunoprecipitated with aFGFR2. The immunoprecipitated samples were subjected to SDS-PAGE (6%) and blotted with αFGFR2 antibodies. The molecular mass of the major form of FGFR2-ROS was approximately 360 kDa, suggesting that this form represents dimers of the minor form (approximately 180 kDa). The minor broad band was converted to a discrete band of 110 kDa by enzymes which digest sugar moieties. Therefore, the minor form may represent the modified monomer of FGFR2.ROS.

Chemical crosslinking was performed on NIH 3T3 transfectants expressing KGFR, which can been activated by KGF secreted by NIH 3T3 cells. A large fraction of KGFR protein was detected as receptor dimers following crosslinker exposure. In the absence of the crosslinker, the majority of KGFR protein was detected in its monomeric form. In contrast, a much lower level of receptor dimers was detected in the case of FGFR2-WT, which cannot be activated by secreted KGF. Interestingly, the mobility of receptor protein in FGFR2-ROS transfectants was unaltered in both crosslinker-treated and untreated cells, suggesting that most of the receptor had already been dimerized. These dimers were very stable, since the larger receptor species were detected in SDS-PAGE under reduced and denatured conditions and were highly phosphorylated on tyrosine. These results may indicate that the C-terminal-encoded sequence of FGFR2-ROS mediates usually stable receptor dimer formation in the absence of ligand. Constitutive dimerization and autophosphorylation may therefore underlie the potent transforming activity of FGFR2-ROS.

The FGFR2 vene is rearranged in ROS cells. To examine if the altered C-terminal domain of FGFR2-ROS was generated by chromosomal rearrangement of the FGFR2 gene in the osteosarcoma cell line, normal rat kidney (NRK) or ROS cell genomic DNA was analyzed by Southern blonting. NRK or ROS cell genomic DNA was digested with BglII, BamHI or SpeI, separated on a 0.7% agarose gel, and transferred to a nylon membrane. The blot was hybridized with a 0.38-kb BglII-HindIII fragment of the FGFR2-WT cDNA that is derived from the 3' one-third of the coding sequence of FGFR2-WT cDNA (amino acids 697–822), which contains regions that are present and regions that are absent in FGFR2-ROS. The probe detected multiple DNA fragments in BglII (8 kb, 4 kb, 3.5 kb), BamHI (10 kb, 7 kb), and SpeI (10.5 kb, 7.5 kb) digests of normal genornic DNA. In contrast, some of these fragments (BglII, 8 kb; BamHI, 7 kb; SpeI, 7.5 kb) were not detected by the same probe in ROS cell genomic DNA, indicating that part of the region detectable by the probe is not present in ROS cell DNA.

Southern blot analysis was also performed using a probe from a region that spans the FGFR2-FRAG1 junction (amino acids 697–764 of FGFR2 and 70 amino acids derived form the fusion partner gene). ROS cell DNA contained several DNA fragments that were not detected in normal cells (e.g., BglII 4 kb, BamHI 8 kb and 6 kb, SpeI 8 kb and 4 kb). Therefore, ROS cells contain DNA fragments that are not present in normal DNA. These results strongly suggest that the FGFR2 gene has undergone a structural rearrangement in ROS cells that occurs in the region encoding the C-terminal domain of the receptor.

Figure 3:
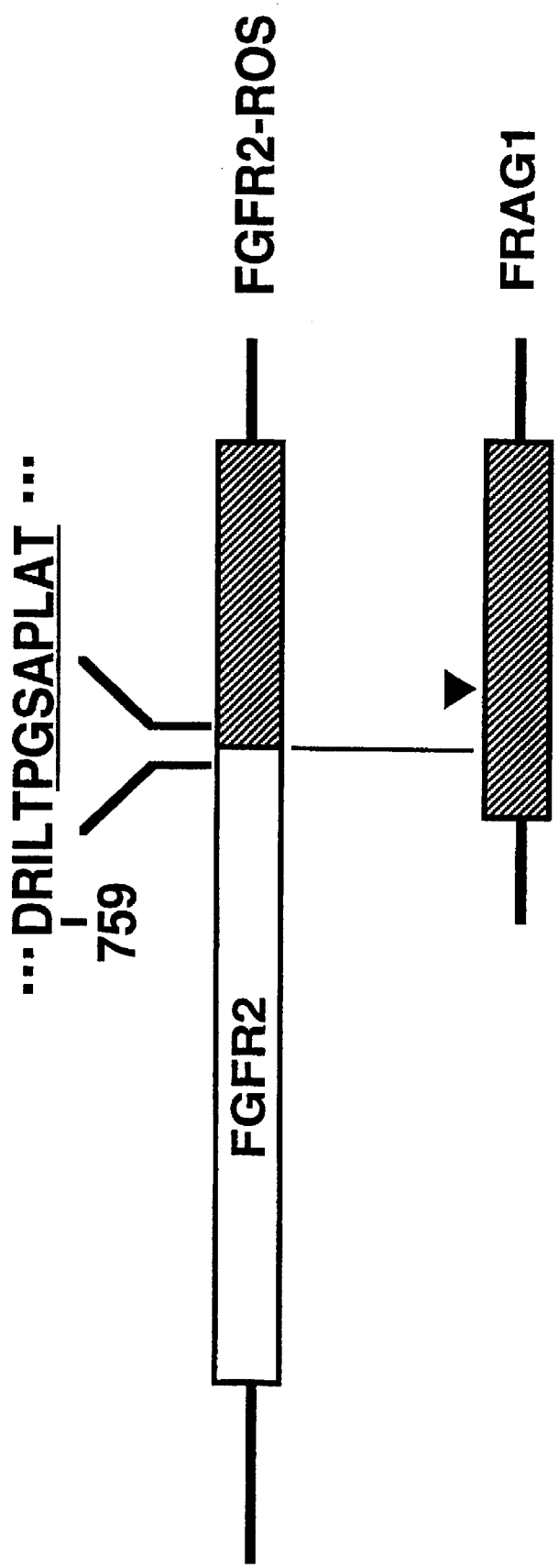
FIG. 3 shows a comparison of FGFR2-ROS and rat FRAG1 cDNAs. The predicted amino acid sequence for FGFR2 (starting at position 759) and rat FRAG1 (underlined) at the fusion junction is shown above the schematic. A vertical line indicates the breakpoint. The first ATG in the open reading frame of rat FRAAG1 is shown by an arrowhead. The portions of FGFR2-ROS derived from rat FRAG1 are indicated by hatched boxes. Untranslated regions are depicted by solid lines.

Cloning and structure of the fusion partner gene, FRAG1. The experiments described above established that FGFR2-ROS was generated by a gene fusion between FGFR2 and a novel gene, which we designate rat FRAG1 (SEQ ID NO 5). Since acquisition of the FRAG1 sequence played a critical role in FGFR2 activation in ROS cells, we isolated cDNA for the wild-type rat FRAG1 gene. A probe derived from the FRAG1 region of FGFR-ROS cDNA was used to screen a rat brain cDNA library. A plasmid with the largest cDNA insert, FRAG1 CL26 (1.6 kb), was chosen for characterization. Since the detection of a 2.0 kb FRAG1 mRNA by northern blot analysis (see below) suggested that the rat FRAG1 clones isolated by library screening have been truncated, additional 5' sequence was obtained by anchored PCR (Frohman et al., Proc. Natl. Acad. Sci. USA 85:8998–9002, 1988). These combined cDNA sequences (1780 bp SEQ ID NO: 5) together constitute a nearly full length rat FRAG1 cDNA (FIG. 3). Analysis of the rat FRAG1 cDNA revealed an open reading frame of 254 amino acids, starting from an ATG codon located at positions 723–725, that encodes a protein with a predicted mass of 28 kDa (FIG. 4 SEQ ID NO 6). An in-frame termination codon is located at positions 334–336. Therefore, the longest open frame starts at 129 amino acids upstream from the first ATG, if any amino acid except methiomne is considered ns a start codon. Comparison of the FGFR1-ROS ad FRAG1 sequences revealed that the breakpoint was located 70 residues amino-terminal from the first ATG, and that the chromosomal rearrangement resulted in an in-frame fusion of both genes. These results indicate that the entire coding sequence of FRAG1 has been fused with FGFR2 in ROS cells to activate the receptor.

Nucleotide and protein data base searches revealed that rat FRAG1 was not identical to any known sequences. FRAG1 gene expression in rat tissues was studied by northern blotting. A blot containing poly(A)$^+$ RNA (2 $\mu$g) from various adult rat tissues was hybridized to a rat FRAG1 cDNA probe. A 2.0 kb rat FRAG1 mRNA was observed in heart, brain, spleen, lung, liver, skeletal muscle, kidney, and testis. In addition, 1.3 kb and 0.9 kb mRNA species were detected by the rat FRAG1 probe in testis and, to a lesser extent in lung. A 3.2 kb mRNA was also detected in lung, brain, spleen, kidney, and testis. Since FRAG1 is not related to any proteins with known functions, it was not possible to presume its function on a structural basis. However, two unknown proteins that showed similarity to FRAG1 were found in protein data bases. These proteins, a 30 kDa protein of the nematode Caenorhabditis elegans (TO4A8.12, Gen-Pept accession number Z35663) and a 107.9 kDa yeast protein (SC108 kD, SwissProt accession number P25618), were deduced from transcription units identified in nematode and yeast genome sequencing projects, respectively, indicating that FRAG1-related genes are well conserved from mammalian to lower eukaryotic cells. FIG. 5 shows an alignment of the 5' ends of rat FRAG1 and corresponding sequences in the 30 kDa nematode and 107.9 kDa yeast genes showing a well-conserved region that is useful, for example, as a hybridization probe. FIG. 6 shows an alignment of the deduced protein sequences of rat FRAG1 and the 30 kDa nematode and 107.9 kDa yeast genes.

Subcellular localization of rat FRAG 1. Altered subcellular localization of receptors can result in their activation (Mitra et al., Proc. Nat. Acad. Sci. USA 84:6707–6711, 1987). Therefore, immunofluorescence staining of FGFR2-WT and FGFR2-ROS transfectants using αFGFR2 antibody was performed. Both of the receptor species were highly expressed in all subcellular compartments, but expression of FGFR2-ROS in the cytoplasm was slightly less abundant than FGFR2-WT. To examine whether the FRAG1 sequence in FGFR2-ROS affects the subcellular localization of the receptor, immunofluorescence staining of NIH 3T3 cells expressing epitope-tagged FRAG1 was performed. Little staining was observed in NIH 3T3 cells transfected with vector alone (pCEV29F3), indicating a low background of this system. In contrast, a strong signal was observed when immunofluorescence staining was performed on F3-FRAG1 transfectants. In a large fraction of these cells, F3-tagged FRAG1 showed a perinuclear staining pattern consistent with a localization in the Golgi complex. In addition to this perinuclear localization, a subpopulation of cells also exhibited cytoplasmic staining, suggesting that FRAG1 is translocated to the cytoplasm. These results may indicate that the presence of FRAG1 in FGFR2-ROS affects its subcellular localization, which may contribute to the highly activated state of FGFR2-ROS. The identification of FRAG1-like sequences in other species, ubiquitous expression of FRAG1 in adult tissues and perinuclear localization of FRAG1 protein suggest an important role for this gene in cellular functions.

Example 2

Subcellular Localization of FGFR2-ROS (FGFR2-FRAG1)

Immunofluorescent staining of epitope-tagged rat FRAG1 protein revealed a discrete perinuclear subcellular localization. We reasoned that the presence of the FRAG1 sequence on the FGFR2-ROS variant could alter the location of the receptor. When the same experiments were performed on cells transfected with the FGFR2-ROS and FGFR2-WT receptors, we found that the FGFR2-ROS receptor showed a perinuclear staining similar to FRAG1 while the wild-type receptor exhibited a staining consistent with staining on the cell surface.

These results indicate that the presence of the FRAG1 sequence on the FGFR2 alters the subcellular localization of the receptor, which may underlie the potent transforming activity of this receptor variant.

Example 3

Preparation of Anti-FRAG1 Antibodies

Two peptides derived from the predicted protein sequence of rat FRAG1 were used to generate antisera against FRAG1 protein. These peptides were synthesized as MAP peptides which consist of a core residue from which four arms of identical peptides are produced. The generation of such peptides obviates the need to couple the peptides to a carrier protein to enhance antigenicity. The resulting peptides, N-FRAG1 resides 1–16 of SEQ ID NO 6 and C-FRAG1 resides 240–254 of SEQ ID NO: 6, were injected into rabbits to generate anti-FRAG1 antibodies. These antisera recognized a 28 kDa protein in both untransfected (endogenous) and FRAG1-transfected (overexpressing) cells.

Example 4

Isolation of Human FRAG1

We have isolated the human homolog of rat FRAG1. A cDNA library prepared from human fibroblast cells, M426, was screened with a rat FRAG1 cDNA probe. Positive plaques were rescreened two additional times to ensure the identity and purity of the clones. Five positive clones were identified with inserts in the ranging from 1.5 kb to 1.8 kb. Internal DNA sequence revealed that these cDNAs encoded the human homolog of rat FRAG1. The cDNA containing the largest insert, hFRAG1-5CA, was chosen to determine the entire DNA sequence.

Over 90% of the human FRAG1 sequence has now been determined (FIG. 7, SEQ ID NO 1). A search of nucleotide sequence databases revealed that human FRAG1 is highly related to the rat FRAG1 sequence but contains unique regions not present in the rat FRAG1 sequence. The size of the human FRAG1 mRNA on Northern blots suggest that the human FRAG1-5CA clone is full length.

Example 5

Isolation of Genomic Clones and Homologs of Rat and Human FRAG1

The skilled artisan can obtain the genomic clones for rat and human FRAG1 by screening genomic libraries with the respective cDNA sequences (or fragments thereof) as probes or primers under high stringency hybridization conditions using conventional nucleic acid hybridization techniques.

In order to obtain a FRAG1 homolog from a species other than rat or human, a cDNA (or genomic library) is screened with (1) a nucleic acid probe or primer having complete sequence similarity with either the rat or human FRAG1 cDNA sequence or both (including the respective full-length cDNA(s)); a degenerate nucleic acid probe from a region that is highly conserved between rat and human FRAG1; for expression libraries. an antibody probe that specifically recognizes either rat or human FRAG1 (and preferably both rat and human FRAG1). Appropriate cDNA and genomic libraries, including expression libraries, are widely available and are commercially available from a variety of sources.

Having illustrated and described the principles of the present invention, it should be apparent to persons skilled in the art that the invention can be modified in arrangement and detail without departing from such principles. We claim all modifications that are within the spirit and scope of the appended claims.

---

What is claimed is:

1. An isolated nucleic acid that encodes a polypeptide that, when expressed as an in-frame fusion with a growth factor receptor, forms a stable protein dimer of the receptor, wherein the nucleic acid comprises a sequence encoding a protein having at least 70% amino acid sequence identity to SEQ ID NO 6 or 12.

2. The nucleic acid of claim 1 wherein the nucleic acid encodes a protein having at least 80% sequence identity to SEQ ID NO 6 or 12.

3. The nucleic acid of claim 2 wherein the nucleic acid encodes a protein having at least 90% sequence identity to SEQ ID NO 6 or 12.

4. The nucleic acid of claim 1 wherein the nucleic acid contains silent or conservative substitutions.

5. The nucleic acid of claim 1 wherein the growth factor receptor is fibroblast growth factor receptor 2 (FGFR2).

6. The nucleic acid of claim 1, wherein the nucleic acid comprises a full-length protein-coding region of SEQ ID NO 5 or 11.

7. A cell that comprises the nucleic acid of claim 1.

8. An isolated polypeptide encoded by the nucleic acid of claim 1.

9. An isolated polypeptide according to claim 8 comprising at least 10 consecutive amino acids of SEQ ID NO 6 or 12.

10. An isolated polypeptide according to claim 8 having at least 70% amino acid sequence homology to SEQ ID NO 6 or 12.

11. The isolated nucleic acid of claim 5, wherein the nucleic acid sequence encodes a protein having at least 90% sequence identity to SEQ ID NO 6 or 12.

12. An isolated nucleic acid that encodes a polypeptide that, when expressed as an in-frame fusion with a growth factor receptor, stimulates transforming activity of the growth factor receptor by at least $10^4$ focus forming units per pmol of DNA, wherein the nucleic acid comprises a sequence encoding a protein having at least 70% amino acid sequence identity of SEQ ID NO 6 or 12.

13. The isolated nucleic acid of claim 12, wherein the in-frame fusion with a growth factor receptor stimulates transforming activity of the growth factor receptor by greater than $10^4$ focus forming units per pmol of DNA.

14. The isolated nucleic acid of claim 12, wherein the nucleic acid comprises a sequence encoding a protein having at least 80% amino acid sequence identity to SEQ ID NO 6 or 12.

15. The nucleic acid of claim 14, wherein the nucleic acid comprises a sequence encoding a protein having at least 90% amino acid sequence identity to SEQ ID NO 6 or 12.

16. A cell that comprises the nucleic acid of claim 11.

17. A cell that comprises the nucleic acid of claim 13.

18. A cell that comprises the nucleic acid of claim 15.

19. A cell that comprises the nucleic acid of claim 12.

20. A cell that comprises the nucleic acid of claim 14.

21. A cell that comprises the nucleic acid of claim 12 wherein the growth factor receptor is FGFR2.

22. An isolated polypeptide encoded by the nucleic acid of claim 11.

23. An isolated polypeptide encoded by the nucleic acid of claim 13.

24. An isolated polypeptide encoded by the nucleic acid of claim 15.

25. An isolated polypeptide encoded by the nucleic acid of claim 12.

26. An isolated polypeptide encoded by the nucleic acid of claim 14.

27. A method of producing an isolated FRAG1 polypeptide receptor protein that can form a stable dimer of the receptor in the absence of receptor ligand, the method comprising:

culturing a cell comprising an expression vector that comprises a nucleic acid of claim 1, under conditions suitable for expression of the protein, thereby producing the protein.

28. The method of claim 27, wherein the expression vector comprises the nucleic acid of claim 15.

29. The method of claim 27, wherein the expression vector comprises the nucleic acid of claim 6.

30. The method of claim 27, wherein the expression vector comprises the nucleic acid of claim 11.

31. The method of claim 27, wherein the expression vector comprises the nucleic acid of claim 13.

32. The method of claim 27, wherein the expression vector comprises the nucleic acid of claim 12.

33. The method of claim 27, wherein the expression vector comprises the nucleic acid of claim 14.

34. The isolated polypeptide of claim 10, wherein the polypeptide comprises a sequence having at least 80% amino acid sequence homology to SEQ ID NO 6 or 12.

35. The isolated polypeptide of claim 34, wherein the polypeptide comprises a sequence having at least 95% amino acid sequence homology to SEQ ID NO 6 or 12.

* * * * *

UNITED STATES PATENT AND TRADEMARK OFFICE
CERTIFICATE OF CORRECTION

PATENT NO. : 6,323,316 B1
DATED : November 27, 2001
INVENTOR(S) : Matthew V. Lorenzi and Toru Miki It is certified that error appears in the above-identified patent and that said Letters Patent is hereby corrected as shown below:

Title page,
Item [73], Assignee: "Department of and Human Services, Wsahington, DC (US)" should read -- Department of Health and Human Services, Washington, DC (US) --.

Column 3,
Line 44, "FRAAG1" should read -- FRAG1 --.
Line 63, "T)4A8.12" should read -- T04A8.12 --.

Column 4,
Line 34, "it" should read -- It --.
Line 61, "CPR" should read -- CFR --.

Column 5,
Line 20, "Homolot" should read -- Homolog --.
Line 62, "nueleotideg," should read -- nucleotides, --.
Line 62, "10" should read -- 30 --.

Column 7,
Line 65, "seguence" should read -- sequence --.

Column 10,
Line 3, "*Enymol*" should read -- *Enzymol* --.
Line 25, "chemniluminescent" should read -- chemiluminescent --.

Column 13,
Line 57, "en al.," should read -- et al., --.

Column 16,
Line 26, "FGFR2.ROS" should read -- FGFR2-ROS --.
Line 28, "been" should read -- be --.
Line 51, "blonting" should read -- blotting --.
Line 61, "genormic" should read -- genomic --.

UNITED STATES PATENT AND TRADEMARK OFFICE
CERTIFICATE OF CORRECTION

PATENT NO.   : 6,323,316 B1
DATED        : November 27, 2001
INVENTOR(S)  : Matthew V. Lorenzi and Toru Miki It is certified that error appears in the above-identified patent and that said Letters Patent is hereby corrected as shown below:

Column 17,
Line 34, "methiomne" should read -- methionine --.
Line 34, "ns" should read -- as --.
Line 35, "FGFR1-ROS ad" should read -- FGFR2-ROS and --.

Column 18,
Lines 63-64, "resides" should read -- residues --.

Column 19,
Line 16, "1" should read -- 11 --.

Signed and Sealed this

Eighth Day of October, 2002

*Attest:*

*Attesting Officer*

JAMES E. ROGAN
*Director of the United States Patent and Trademark Office*

SEQUENCE LISTING

<160> NUMBER OF SEQ ID NOS: 12

<210> SEQ ID NO 1
<211> LENGTH: 64
<212> TYPE: PRT
<213> ORGANISM: Rattus sp.

<400> SEQUENCE: 1

```
Asp Arg Ile Leu Thr Leu Thr Thr Asn Glu Glu Tyr Leu Asp Leu Thr
 1               5                  10                  15

Gln Pro Leu Glu Gln Tyr Ser Pro Ser Tyr Pro Asp Thr Arg Ser Ser
            20                  25                  30

Cys Ser Ser Gly Asp Asp Ser Val Phe Ser Pro Asp Pro Met Pro Tyr
        35                  40                  45

Glu Pro Cys Leu Pro Gln Tyr Pro His Ile Asn Gly Ser Val Lys Thr
    50                  55                  60
```

<210> SEQ ID NO 2
<211> LENGTH: 29
<212> TYPE: PRT
<213> ORGANISM: Rattus sp.

<400> SEQUENCE: 2

```
Asp Arg Ile Leu Thr Leu Thr Thr Asn Glu Glu Tyr Leu Asp Leu Ser
 1               5                  10                  15

Gln Pro Leu Glu Pro Tyr Ser Pro Cys Tyr Pro Asp Arg
            20                  25
```

<210> SEQ ID NO 3
<211> LENGTH: 64
<212> TYPE: PRT
<213> ORGANISM: Rattus sp.

<400> SEQUENCE: 3

Asp Arg Ile Leu Thr Pro Gly Ser Ala Pro Leu Ala Thr Gly Val Arg
1               5                   10                  15

Pro Pro Ser His His Tyr Leu Gly Pro Ser Ala Gln Asp Pro Ser Arg
            20                  25                  30

His Cys Gly Trp Arg Arg Gly Gly Ala Leu Glu Pro Gln Thr Ser Phe
        35                  40                  45

Glu Ser Leu Pro Cys Gln Leu Ala Cys Gly Phe Glu Ser Asp Lys Met
    50                  55                  60

<210> SEQ ID NO 4
<211> LENGTH: 13
<212> TYPE: PRT
<213> ORGANISM: Rattus sp.

<400> SEQUENCE: 4

Asp Arg Ile Leu Thr Pro Gly Ser Ala Pro Leu Ala Thr
1               5                   10

<210> SEQ ID NO 5
<211> LENGTH: 1780
<212> TYPE: DNA
<213> ORGANISM: Rattus sp.
<220> FEATURE:
<221> NAME/KEY: CDS
<222> LOCATION: (723)..(1487)

<400> SEQUENCE: 5

```
cgcgcgggca ggtctatggg gagggacgag gagtcccact ctctctgcgg caacggttgg    60
ctgagaaagg gtcatgacgt cacacagggc cctcgaagag ggcaggtgag tggctagagt   120
agtgagcacc aaacagcagt gacgttgggt tcagaccccg cccctttcct ggagcgcgg    180 agactcgcta cggaagcttc ggccaatcag aaggaagacc caaggatgat atggtgatgg   240
catgcagcca gaggtaaaat gacaaggtga cttattcgac atgtcaaaat cttgtttcca   300
gagctctctg actgctctca cgtactcaaa aatagtgggg acagagccga cctggggagg   360
cttggcttca agagacgcta gattataaag aaagccagga gtcccggtcg ccaaaatggg   420
gaggagccag tgaagaaacg ggcccagttt cctctttaag acccacccca gagcgctggc   480
cccgcctcac gccgttgctg ctgcgacccg ccccttcca ctcgcccccg ggctgggctg    540
gggctcccgg ttccgcgccc ctggctacgg gggtacggcc cctagccac cactacttgg    600 ggccttctgc tcaagatccc tccaggcact gcggatggag gcgtggggga gccttggaac   660
ctcagactag ttttgaatcc ctgccctgcc agtcactagc ttgtggcttt gagtctgaca   720
``` ag atg tac cag gtc cca ttg aca ctg gac cgg gat ggg acc cta gtc        767
   Met Tyr Gln Val Pro Leu Thr Leu Asp Arg Asp Gly Thr Leu Val
   1               5                   10                  15 cgg ctc cgc ttc act atg gtg gcc ctg atc acg gtc tgc tgt cca ctt       815
Arg Leu Arg Phe Thr Met Val Ala Leu Ile Thr Val Cys Cys Pro Leu
                20                  25                  30 gtc gcc ttc ttc ttc tgc atc ctg tgg tcc ctg ctc ttc cac ttc aag       863
Val Ala Phe Phe Phe Cys Ile Leu Trp Ser Leu Leu Phe His Phe Lys
            35                  40                  45 gag aca aca tct aca cac tgt ggg gtg ccc aat tac ctg cca tca gtg       911
Glu Thr Thr Ser Thr His Cys Gly Val Pro Asn Tyr Leu Pro Ser Val
        50                  55                  60 agc tct gcc att ggt ggg gag gtt ccc cag cgc tac gtg tgg cgt ttc       959
Ser Ser Ala Ile Gly Gly Glu Val Pro Gln Arg Tyr Val Trp Arg Phe

```
                   65                  70                  75
tgc att ggc ctg cac tcg gca ccc cgc ttc ttg aca gcc ttc gcc tat     1007
Cys Ile Gly Leu His Ser Ala Pro Arg Phe Leu Thr Ala Phe Ala Tyr
 80                  85                  90                  95 tgg aac cac tac ctc agc tgt gca tcc ccg tgc ccg gtc tac cgc ctt     1055
Trp Asn His Tyr Leu Ser Cys Ala Ser Pro Cys Pro Gly Tyr Arg Leu
                100                 105                 110 ctc tgc cgc cta cac ttc agt ctc aat gtg gtg gag aac ctg gca ctg     1103
Leu Cys Arg Leu His Phe Ser Leu Asn Val Val Glu Asn Leu Ala Leu
            115                 120                 125 ctc gtg ctc acc tat gtc tcc tcc tcc gag gac ttc acc atc cat gaa     1151
Leu Val Leu Thr Tyr Val Ser Ser Ser Glu Asp Phe Thr Ile His Glu
        130                 135                 140 aat gct ttc att gtg ttt atc gcg gcc tcc ctc agt tac atg ctc ctc     1199
Asn Ala Phe Ile Val Phe Ile Ala Ala Ser Leu Ser Tyr Met Leu Leu
    145                 150                 155 acc tgc att ctc tgg cgg ctg acc aag aag cac aca gat cgc aag tcc     1247
Thr Cys Ile Leu Trp Arg Leu Thr Lys Lys His Thr Asp Arg Lys Ser
160                 165                 170                 175 tac agc tgg aaa caa cgg ctc ttc atc atc aac ttc atc tcc ttc ttc     1295
Tyr Ser Trp Lys Gln Arg Leu Phe Ile Ile Asn Phe Ile Ser Phe Phe
                180                 185                 190 tcg gcg ctg gct gtt tac ttc cgg cac aac atg tat tgt gag gct gga     1343
Ser Ala Leu Ala Val Tyr Phe Arg His Asn Met Tyr Cys Glu Ala Gly
            195                 200                 205 gtg tac acc atc ttt gcc atc ctg gag tac act gtg gtc cta acc aac     1391
Val Tyr Thr Ile Phe Ala Ile Leu Glu Tyr Thr Val Val Leu Thr Asn
        210                 215                 220 atg gcg ttc cac atg aca gcc tgg tgg gac ttc ggg aac aaa gag ctg     1439
Met Ala Phe His Met Thr Ala Trp Trp Asp Phe Gly Asn Lys Glu Leu
    225                 230                 235 cta ata acc tct cag cct ggg aaa aga gat tct aaa ccc cgt ctc tga     1487
Leu Ile Thr Ser Gln Pro Gly Lys Arg Asp Ser Lys Pro Arg Leu
240                 245                 250                 255 tcctggaaaa caagaaacca ctctggcctt ccctatctca gtgtcctctc tgggcccttc     1547
tccgtctggg gactgggaga gaagagcagg aagggtagga caaggctgac cccagcactg     1607
ctgacttctc cccccctctc atctctcatg ggggtcttca agaagcatca ctactcactg     1667
aaaggtccta aaaagctgag ctggcaggaa agccctacca cttggtgcta agaaaaaaaa     1727
aaaaaaaaaa aaaaaaaaaa aaaaaaaaaa aaaaaaaaaa aaaaaaaaaa aaa            1780

<210> SEQ ID NO 6
<211> LENGTH: 254
<212> TYPE: PRT
<213> ORGANISM: Rattus sp.

<400> SEQUENCE: 6

Met Tyr Gln Val Pro Leu Thr Leu Asp Arg Asp Gly Thr Leu Val Arg
 1               5                  10                  15

Leu Arg Phe Thr Met Val Ala Leu Ile Thr Val Cys Cys Pro Leu Val
                20                  25                  30

Ala Phe Phe Cys Ile Leu Trp Ser Leu Leu Phe His Phe Lys Glu
            35                  40                  45

Thr Thr Ser Thr His Cys Gly Val Pro Asn Tyr Leu Pro Ser Val Ser
        50                  55                  60

Ser Ala Ile Gly Gly Glu Val Pro Gln Arg Tyr Val Trp Arg Phe Cys
65                  70                  75                  80
```

-continued

```
Ile Gly Leu His Ser Ala Pro Arg Phe Leu Thr Ala Phe Ala Tyr Trp
             85                  90                  95

Asn His Tyr Leu Ser Cys Ala Ser Pro Cys Pro Gly Tyr Arg Leu Leu
            100                 105                 110

Cys Arg Leu His Phe Ser Leu Asn Val Val Glu Asn Leu Ala Leu Leu
            115                 120                 125

Val Leu Thr Tyr Val Ser Ser Glu Asp Phe Thr Ile His Glu Asn
            130                 135                 140

Ala Phe Ile Val Phe Ile Ala Ala Ser Leu Ser Tyr Met Leu Leu Thr
145                 150                 155                 160

Cys Ile Leu Trp Arg Leu Thr Lys Lys His Thr Asp Arg Lys Ser Tyr
            165                 170                 175

Ser Trp Lys Gln Arg Leu Phe Ile Ile Asn Phe Ile Ser Phe Phe Ser
            180                 185                 190

Ala Leu Ala Val Tyr Phe Arg His Asn Met Tyr Cys Glu Ala Gly Val
            195                 200                 205

Tyr Thr Ile Phe Ala Ile Leu Glu Tyr Thr Val Val Leu Thr Asn Met
            210                 215                 220

Ala Phe His Met Thr Ala Trp Trp Asp Phe Gly Asn Lys Glu Leu Leu
225                 230                 235                 240

Ile Thr Ser Gln Pro Gly Lys Arg Asp Ser Lys Pro Arg Leu
            245                 250
```

<210> SEQ ID NO 7
<211> LENGTH: 46
<212> TYPE: DNA
<213> ORGANISM: Caenorhabditis elegans

<400> SEQUENCE: 7
ttatctcttc tactgcactt tgatcaggca acatctacac attgtg          46

<210> SEQ ID NO 8
<211> LENGTH: 46
<212> TYPE: DNA
<213> ORGANISM: Saccharomyces cerevisiae

<400> SEQUENCE: 8
tctactgttc agctgcacac gcaacaccct actacaacac aatgtc          46

<210> SEQ ID NO 9
<211> LENGTH: 245
<212> TYPE: PRT
<213> ORGANISM: Caenorhabditis elegans

<400> SEQUENCE: 9

```
Gln Arg Ser Ala Asp Trp Met Ala Phe Gly Asp Asp Ile Leu Ser
  1               5                  10                  15

Ile Pro Phe Lys Tyr Phe Val Ile Cys Ile Gly Gly Leu Pro Ser Ser
             20                  25                  30

Ala Leu Leu Ile Cys Val Ile Leu Ser Leu Leu His Phe Asp Gln
             35                  40                  45

Ala Thr Ser Thr His Cys Glu Val Ala Asn Trp Leu Pro Ser Ile Ser
       50                   55                  60

Ala Ala Val Ser Ile Tyr Thr Pro Glu Lys Tyr Ile Trp Arg Ile Leu
65                   70                  75                  80

Ile Gly Leu His Ile Gly Pro Arg Leu Val Val Ala Ile Ala Phe Arg
             85                  90                  95
```

```
Asn Phe Leu Leu Arg Phe Leu Cys Asn Leu Ala Cys Phe Leu Asn Leu
                100                 105                 110

Leu Glu Asn Phe Phe Leu Leu Ala Leu Thr Ser Ile Ser Ser Ser Glu
            115                 120                 125

Asp His Ser Leu His Ala Lys Cys Phe Gly Gly Phe Ala Ile Cys Ser
        130                 135                 140

Ile Ile Tyr Met Leu Leu Ser Thr Trp Leu Arg Arg Thr Ala Thr Asn
145                 150                 155                 160

Leu Gly Gly Arg Ser His Glu Tyr Lys Ile Leu Gly Ala Ala Ile Phe
                165                 170                 175

Val Leu Cys Phe Phe Leu Gly Ala Tyr Leu Tyr Trp Arg His Asn Thr
            180                 185                 190

Tyr Cys Glu Pro Gly Ile Tyr Thr Leu Phe Ala Leu Val Glu Tyr Ser
        195                 200                 205

Ala Val Leu Ser Asn Ile Phe Phe His Cys Thr Leu Tyr Tyr Asp Phe
    210                 215                 220

His Gly Lys Asn Ile Val Leu Thr Ser Ser Phe Gly Gly His Tyr
225                 230                 235                 240

Asn Leu Leu Pro Thr
                245

<210> SEQ ID NO 10
<211> LENGTH: 183
<212> TYPE: PRT
<213> ORGANISM: Saccharomyces cerevisiae

<400> SEQUENCE: 10

Tyr Ser Leu His Phe His Lys Ile Val Thr Asn Ala His Tyr Thr Tyr
  1               5                  10                  15

Pro Asp Glu Trp Phe Pro Ser Val Ser Ala Thr Ile Gly Asp Arg Tyr
               20                  25                  30

Pro Glu Arg Ser Ile Phe Gln Ile Leu Ile Ala Leu Thr Ala Phe Pro
            35                  40                  45

Arg Phe Leu Leu Leu Gly His Tyr Tyr Leu Asn Gln Ser Lys Val
     50                  55                  60

Cys Phe Leu Val Gly Val Leu Arg Thr Val Ser Cys Gly Gly Trp Val
 65                  70                  75                  80

Tyr Ile Thr Ser Thr Asp Asp His Asp Ile His Asp Ile Phe Met Ile
                 85                  90                  95

Thr Tyr Ile Val Leu Thr Leu Pro Trp Asp Ile Met Ile Thr Arg Tyr
                100                 105                 110

Ser Ser Pro Leu Thr Ser Lys Asn Lys Gly Leu Thr Ala Thr Ile Phe
            115                 120                 125

Phe Gly Thr Leu Phe Pro Met Ile Tyr Trp Tyr Ile Gln His Ser Val
        130                 135                 140

Gln Gln Arg Ala Gly Ala Tyr Ser Ile Tyr Ala Tyr Phe Glu Trp Ser
145                 150                 155                 160

Leu Ile Leu Leu Asp Ile Ala Phe Asp Ala Phe Ala Tyr Ala Asp Phe
                165                 170                 175

Lys Lys Ile Asp Ile Val Leu
            180

<210> SEQ ID NO 11
<211> LENGTH: 1648
<212> TYPE: DNA
<213> ORGANISM: Homo sapiens
```

```
<220> FEATURE:
<221> NAME/KEY: CDS
<222> LOCATION: (113)..(1060)

<400> SEQUENCE: 11
aaaacccgcc gttcgcgctc tgaccagccc gcagagccag ccccgaccc cgggccacct      60 gggccccgg gttccgccgg cactctcgcc accaccgcgt gggtctgaca ag atg tac    118
                                                          Met Tyr
                                                            1 cag gtc cca cta cca ctg gat cgg gat ggg acc ctg gta cgg ctc cgc     166
Gln Val Pro Leu Pro Leu Asp Arg Asp Gly Thr Leu Val Arg Leu Arg
        5                  10                  15 ttc acc atg gtg gcc ctg gtc acg gtc tgc tgt cca ctt gtc gcc ttc     214
Phe Thr Met Val Ala Leu Val Thr Val Cys Cys Pro Leu Val Ala Phe
 20                  25                  30 ctc ttc tgc atc ctc tgg tcc ctg ctc ttc cac ttc aag gag aca acg     262
Leu Phe Cys Ile Leu Trp Ser Leu Leu Phe His Phe Lys Glu Thr Thr
 35                  40                  45                  50 gcc aca cac tgt ggg gcc acg ccc tgc agg atg ttc tct gcg gcc tcc     310
Ala Thr His Cys Gly Ala Thr Pro Cys Arg Met Phe Ser Ala Ala Ser
                 55                  60                  65 cag cct ttg gac ccc gat ggg acc ttg ttc cgg ctt cgc ttc aca gcc     358
Gln Pro Leu Asp Pro Asp Gly Thr Leu Phe Arg Leu Arg Phe Thr Ala
         70                  75                  80 atg gtc tgg tgg gcc atc act ttt cct gtg ttc ggc ttc ttc ttc tgc     406
Met Val Trp Trp Ala Ile Thr Phe Pro Val Phe Gly Phe Phe Phe Cys
             85                  90                  95 atc atc tgg tcc ctg gtg ttc cac ttt gag tac acg gtg gcc act gac     454
Ile Ile Trp Ser Leu Val Phe His Phe Glu Tyr Thr Val Ala Thr Asp
100                 105                 110 tgt ggg gtg ccc aat tac ctg ccc tcg gtg agc tca gcc atc ggc ggg     502
Cys Gly Val Pro Asn Tyr Leu Pro Ser Val Ser Ser Ala Ile Gly Gly
115                 120                 125                 130 gag gtg ccc cag cgc tac gtg tgg cgt ttc tgc atc ggc ctg cac tcg     550
Glu Val Pro Gln Arg Tyr Val Trp Arg Phe Cys Ile Gly Leu His Ser
                135                 140                 145 gcg cct cgc ttc ttg gtg gcc ttc gcc tac tgg aac cac tac ctc agc     598
Ala Pro Arg Phe Leu Val Ala Phe Ala Tyr Trp Asn His Tyr Leu Ser
            150                 155                 160 tgc acc tcc ccg tgt tcc tgc tat cgc ccg ctc tgc cgc ctc aac ttc     646
Cys Thr Ser Pro Cys Ser Cys Tyr Arg Pro Leu Cys Arg Leu Asn Phe
        165                 170                 175 ggc ctc aat gtc gtg gag aac ctc gcg ttg cta gtg ctc act tat gtc     694
Gly Leu Asn Val Val Glu Asn Leu Ala Leu Leu Val Leu Thr Tyr Val
    180                 185                 190 tcc tcc tcc gag gac ttc acc atc cac gaa aat gct ttc att gtg ttc     742
Ser Ser Ser Glu Asp Phe Thr Ile His Glu Asn Ala Phe Ile Val Phe
195                 200                 205                 210 att gcc tca tcc ctc ggg cac atg ctc ctc acc tgc att ctc tgg cgg     790
Ile Ala Ser Ser Leu Gly His Met Leu Leu Thr Cys Ile Leu Trp Arg
                215                 220                 225 ttg acc aag aag cac aca gta agt cag gag gat cgc aag tcc tac agc     838
Leu Thr Lys Lys His Thr Val Ser Gln Glu Asp Arg Lys Ser Tyr Ser
            230                 235                 240 tgg aaa cag cgg ctc ttc atc atc aac ttc atc tcc ttc ttc tcg gcg     886
Trp Lys Gln Arg Leu Phe Ile Ile Asn Phe Ile Ser Phe Phe Ser Ala
        245                 250                 255 ctg gct gtc tac ttt cgg cac aac atg tat tgt gag gct gga gtg tac     934
Leu Ala Val Tyr Phe Arg His Asn Met Tyr Cys Glu Ala Gly Val Tyr
    260                 265                 270
```

-continued

```
acc atc ttt gcc atc ctg gag tac act gtt gtc tta acc aac atg gcg      982
Thr Ile Phe Ala Ile Leu Glu Tyr Thr Val Val Leu Thr Asn Met Ala
275                 280                 285                 290 ttc cac atg acg gcc tgg tgg gac ttc ggg aac aag gag ctg ctc ata     1030
Phe His Met Thr Ala Trp Trp Asp Phe Gly Asn Lys Glu Leu Leu Ile
                295                 300                 305 acc tct cag cct gag gaa aag cga ttc tga acccttcagt cctgcttggg      1080
Thr Ser Gln Pro Glu Glu Lys Arg Phe
            310                 315 aggacgcagc ccactgccca gaaacaagaa acacgatacc attctggcct tccccacccc  1140
acatcctctc ttggccttac tgaagatggg ggaagggtaa gaaggaaggg tgtaggccaa  1200
ggctcacccc agtgctgctg gcttctcctc tccacccctc atatgggcgt ggggtcctca  1260
aacatcacct ttacctgaga ggccccaaga agctgagctg cagagagct ccaccatttg   1320 gtgctaaaaa aaaaaacgtc ctgaggttca tgaccaccat ccagtttctg gcctttacac  1380
agtcaccttt cactgaggtc aggagcccct gagcagtggc tgctccctga caaccacagc  1440
catttctctg cacggggtc attcatagga ctaatgtatt tcatgatcta ctgtgcacat   1500
ccaggcctgt ggccacagtc ccctgctaaa gttgctcagg tgttctagtc ctgacttcac  1560 cttttgatt tggtgtgtgc cctagggtat gtacccttcc ccatctgagc ctcggtgtgt   1620
ccatgtgtct ggcgggggat gggtggac                                    1648
```

<210> SEQ ID NO 12
<211> LENGTH: 315
<212> TYPE: PRT
<213> ORGANISM: Homo sapiens

<400> SEQUENCE: 12

```
Met Tyr Gln Val Pro Leu Pro Leu Asp Arg Asp Gly Thr Leu Val Arg
 1               5                  10                  15

Leu Arg Phe Thr Met Val Ala Leu Val Thr Val Cys Cys Pro Leu Val
                20                  25                  30

Ala Phe Leu Phe Cys Ile Leu Trp Ser Leu Leu Phe His Phe Lys Glu
            35                  40                  45

Thr Thr Ala Thr His Cys Gly Ala Thr Pro Cys Arg Met Phe Ser Ala
        50                  55                  60

Ala Ser Gln Pro Leu Asp Pro Asp Gly Thr Leu Phe Arg Leu Arg Phe
65                  70                  75                  80

Thr Ala Met Val Trp Trp Ala Ile Thr Phe Pro Val Phe Gly Phe Phe
                85                  90                  95

Phe Cys Ile Ile Trp Ser Leu Val Phe His Phe Glu Tyr Thr Val Ala
            100                 105                 110

Thr Asp Cys Gly Val Pro Asn Tyr Leu Pro Ser Val Ser Ser Ala Ile
        115                 120                 125

Gly Gly Glu Val Pro Gln Arg Tyr Val Trp Arg Phe Cys Ile Gly Leu
    130                 135                 140

His Ser Ala Pro Arg Phe Leu Val Ala Phe Tyr Trp Asn His Tyr
145                 150                 155                 160

Leu Ser Cys Thr Ser Pro Cys Ser Cys Tyr Arg Pro Leu Cys Arg Leu
                165                 170                 175

Asn Phe Gly Leu Asn Val Val Glu Asn Leu Ala Leu Leu Val Leu Thr
            180                 185                 190

Tyr Val Ser Ser Ser Glu Asp Phe Thr Ile His Glu Asn Ala Phe Ile
        195                 200                 205
```

-continued

```
Val Phe Ile Ala Ser Ser Leu Gly His Met Leu Leu Thr Cys Ile Leu
    210                 215                 220

Trp Arg Leu Thr Lys Lys His Thr Val Ser Gln Glu Asp Arg Lys Ser
225                 230                 235                 240

Tyr Ser Trp Lys Gln Arg Leu Phe Ile Ile Asn Phe Ile Ser Phe Phe
                245                 250                 255

Ser Ala Leu Ala Val Tyr Phe Arg His Asn Met Tyr Cys Glu Ala Gly
                260                 265                 270

Val Tyr Thr Ile Phe Ala Ile Leu Glu Tyr Thr Val Val Leu Thr Asn
        275                 280                 285

Met Ala Phe His Met Thr Ala Trp Trp Asp Phe Gly Asn Lys Glu Leu
    290                 295                 300

Leu Ile Thr Ser Gln Pro Glu Glu Lys Arg Phe
305                 310                 315
```